(12) United States Patent
Huang et al.

(10) Patent No.: US 6,277,625 B1
(45) Date of Patent: Aug. 21, 2001

(54) TRANSGENIC STRAINS OF PSEUDOMONAS FOR BIOCONTROL OF PLANT ROOT DISEASES

(75) Inventors: Zhengyu Huang, Carmel, IN (US); Linda S. Thomashow; Dmitri V. Mavrodi, both of Pullman, WA (US); Jos M. Raaijmakers, Bennekom (NL); David M. Weller; R. James Cook, both of Pullman, WA (US)

(73) Assignees: The United States of America as represented by the Secretary of Agriculture, Washington, DC (US); Washington State University Research Foundation, Pullman, WA (US)

( * ) Notice: Subject to any disclaimer, the term of this patent is extended or adjusted under 35 U.S.C. 154(b) by 0 days.

(21) Appl. No.: 08/994,035

(22) Filed: Dec. 18, 1997

Related U.S. Application Data

(63) Continuation-in-part of application No. 08/974,938, filed on Nov. 20, 1997.

(51) Int. Cl.[7] .............................. C12N 15/78; C12N 1/21; A01N 63/00; A01N 37/18

(52) U.S. Cl. ...................... 435/253.3; 435/471; 435/481; 435/478; 435/252.34; 435/876; 424/164.1; 424/93.47; 424/93.2; 514/2

(58) Field of Search .............................. 435/253.3, 69.1, 435/71.1, 471, 481, 478, 252.34, 243, 876; 424/164.1, 93.47, 93.2; 514/2

(56) References Cited

PUBLICATIONS

Pierson et al. Molecular Plant Microbe Interaction. 1992. vol. 5: 330–339.*

Williams et al. Nucleic acid Research. 1990. vol. 18: 6531–6535.*

P. Shanahan, D.J. O'Sullivan, P. Simpson, J.D. Glennon and F. O'Gara, "Isolation of 2,4–Diacetylphloroglucinol from a Fluorescent Pseudomonad and Investigation of Physiological Parameters Influencing Its Production," *Applied and Environmental Microbiology* 58:353–358 (1992).

H. Hara, M. Bangera, D.–S. Kim, D.M. Weller and L.S. Thomashow, "Effect of transfer and expression of antibiotic biosynthesis genes on biological control activity of fluorescent pseudomonas," In *Improving Plant Productivity with Rhizosphere Bacteria*, Eds. M.H. Ryder, P.M. Stephens, and G.D. Bowen, CSIRO Division of Soils, Adelaide, Australia, Part 4 pp. 247–249 (1994).

* cited by examiner

*Primary Examiner*—David T. Fox
*Assistant Examiner*—Ousama Zaghmout
(74) *Attorney, Agent, or Firm*—Margaret A. Connor; M. Howard Silverstein; John D. Fado

(57) ABSTRACT

Transgenic fluorescent Pseudomonas spp. are described which have a biosynthetic locus which encodes for the production of the antibiotic phenazine-1-carboxylic acid stably introduced into the genome, have a locus which encodes for the production of the antibiotic 2,4-diacetylphloroglucinol, and are effective for control of diseases caused by the soil-borne fungus, Rhizoctonia. Strains are also described which control diseases caused by *Gaeumannomyces graminis* or Pythium, in addition to Rhizoctonia, or have the ability to control all three diseases.

23 Claims, 3 Drawing Sheets

TRANSGENIC STRAINS OF PSEUDOMONAS FOR BIOCONTROL OF PLANT ROOT DISEASES

This application is a continuation-in-part of pending application Ser. No. 08/974,938, filed Nov. 20, 1997.

BACKGROUND OF THE INVENTION

1. Field of the Invention

The present invention relates to biocontrol of plant root diseases. In particular, the invention relates to strains of fluorescent Pseudomonas species which have a biosynthetic locus which encodes for the production of the antibiotic phenazine-1-carboxylic acid stably introduced into the genome, and have biocontrol activity for control of plant root diseases, in particular, diseases caused by the soil-borne pathogen, Rhizoctonia. The invention further relates to methods of making the transgenic strains, and application thereof to control plant root diseases.

2. Description of the Art

Root diseases caused by Rhizoctonia, Pythium, and *Gaeumannomyces graminis*, cause a significant adverse impact on the production of important crops worldwide. The root disease take-all, caused by *Gaeumannomyces graminis* var. *tritici* (Ggt), Rhizoctonia root rot, caused by *Rhizoctonia solani* and *R. oryzae*, and Pythium root rot caused by any of several Pythium species, notably, *Pythium ultimum* and *P. irregulare*, are important root diseases of small grain crops, e.g., wheat, barley, triticale, and rye, worldwide.

Rhizoctonia, a member of the basidiomycotina class of fungi, causes root and stem rot on most food, fiber, and ornamental plants throughout the world, including small grain crops, turf grass, asparagus, canola, corn, sugarbeet, tomatoes, potatoes, peas, rice, beans, soybeans, strawberries, zucchini, and cotton. Root rot on small grain crops caused by Rhizoctonia occurs throughout the United States Pacific Northwest, in Australia, and South Africa, and potentially throughout the temperate regions of the world wherever small grains are grown, especially if grown with reduced or notillage (direct drilling). Rhizoctonia root rot caused by *R. solani* AG8 begins as brown cankerous lesions on the seminal and crown roots that eventually girdles and then severs the roots. Plants with roots pruned off by this disease remain stunted and eventually die without making heads. The disease tends to affect plants in patches and has given rise to other names, such as bare patch disease, purple patch, crater disease, and barley stunt disorder. Of all small grain crops, barley is especially susceptible to *R. solani* AG8. *Rhizoctonia oryzae* infects the embryos of germinating seeds, preventing germination or limiting the formation of seminal roots to only one or two when healthy seedlings produce five or six seminal roots. These two Rhizoctonia species, together with *Rhizoctonia cerealis* and possibly other Rhizoctonia species occur as different mixtures, depending on the soil, cropping systems, weed management practices, and possibly other factors not yet identified.

The soil-borne pathogen complex of Pythium spp. comprises a group of fungi that are among the most successful of all microbial colonists in agricultural soils. It is estimated that nearly all cultivated soil in the world contains spores of at least one, two, three, and even as high as ten Pythium species. Pythium, a member of the oomycetes class of fungi, like Rhizoctonia, affects virtually all food, fiber, and ornamental plants throughout the world. Examples of these plants are given above. Pythium damage to small grains begins as embryo infections and associated poor emergence or stand establishment and continues as destruction of the fine lateral rootlets and root hairs. Plants with Pythium root rot have the appearance of plants without enough fertilizer, because the disease limits the absorptive capacity of the root system through destruction of fine rootlets and root hairs. There are several species of Pythium with ability to attack cereals, either embryos of germinating seeds, root tips and fine rootlets, or all of these delicate and usually juvenile or meristematic tissues.

Widespread diseases of small grain crops and turf grass are caused by the soil-borne fungus *Gaeumannomyces graminis* (Gg), a member of the ascomycotina class of fungi, and result in significant economic losses due to reductions in crop yield. Take-all, a disease caused by *Gaeumannomyces graminis* var. *tritici* (Ggt) occurs in all wheat-growing regions of the world and is probably the most important root disease of wheat and related small grains worldwide. Symptoms of wheat take-all include dark longitudinal lesions on roots; in severe cases, the entire root may become blackened with disease with the fungus migrating to the crown of the wheat plant (where the crown roots originate) and the tillers (stems). Severely infected wheat plants are identified in the field by their white heads which result when infection of the crown by the fungus cuts off water transport to upper plant parts causing the plant to die prematurely. Yield losses can be considerable up to 50% of the potential wheat yield. There are no resistant wheat cultivars and registered fungicides perform inconsistently. Further, growers are being increasingly challenged to grow wheat with minimum or no tillage to reduce soil erosion. These practices increase the severity of take-all and other root diseases. Although wheat is particularly susceptible to the take-all fungus, many other Gramineae such as barley, rye, and triticale can also be infected.

Traditionally, take-all has been controlled by a combination of crop rotation and tillage, practices which reduce the inoculum potential of the pathogen. However, because long rotations are often not economically feasible and tillage contributes to soil erosion, the trend in cereal production is toward less tillage and two or three wheat crops before a break. Both of these practices exacerbate take-all. There is no known source of genetic resistance in wheat against take-all, and methods of chemical control are limited. The need for agriculture to become more sustainable and less dependent on chemical pesticides has necessitated the development of alternative approaches to control take-all and other soil-borne diseases.

Other Gg fungi, for example, *Gaeumannomyces graminis* var. *avenae* (Gga) infects oats and grasses and have been identified as causing take-all patch in turf grasses such as bent grass. *Gaeumannomyces graminis* var. *graminis* (Ggg) infects some grases and has been suggested as causing crown sheath rot in rice.

The pathogens responsible for takeall and Rhizoctonia root rot survive as hyphae or mycelium in the tissues of host plants colonized through their parasitic activities. Pythium species survive in soil as thick-walled oospores or sporangia produced from nutrients robbed from the plant through parasitism. Usually, all three diseases develop simultaneously on the same plants, although one root disease may dominate.

Although Pythium species are ubiquitous in agricultural soils cropped to small grains, damage to small grains caused by Pythium species, e.g., reduction in seedling emergence and plant vigor, is greatest in soils kept wet, especially if the soils are also naturally high in clay content and with pH values below 6.0. Allowing volunteer cereals (plants that develop from seed spilled or dropped by the harvester on the soil surface) to grow in the field after harvest of one crop until only 1 or 2 days before planting the next crop, then spraying with an herbicide such as glyphosate (Round-up®, Monsanto), controls the weeds but greatly favors Pythium root rot and Rhizoctonia root rot. Planting wheat directly into the standing stubble of a previous wheat crop with soil kept moist by sprinkler irrigation or leaving the soil covered with straw favors all three root diseases.

Wheat and other cereals with root disease yield poorly and return less on investments to the grower. Plants with these root diseases also compete poorly with weeds, thereby making it necessary to spend more on herbicides to control weeds. Small grains with root diseases also leave fertilizer unused in the soil, including nitrates, which then may move by leaching below the rooting zone and eventually into ground water. Growers throughout the world continue to use some form of tillage for production of small grains, largely because tillage helps control these root diseases. Tillage causes soils to be more vulnerable to soil erosion. It also requires more energy, and leads to greater evaporation of water needed for yield. Some farmers, attempting to use no-till, burn the stubble in their fields in the belief that this will provide some relief from root diseases. Stubble burning is both environmentally detrimental and socially unacceptable, especially to people in urban areas and cities that object to having to breathe the smoke produced by stubble burning.

Many diseases of wheat, barley, and other crops are controlled by breeding varieties of the crops with resistance to the pathogens. However, this approach has worked mainly for leaf diseases but not for root diseases of wheat, barley, triticale or rye. The only known source of resistance to take-all and Rhizoctonia root rot is in a very distant diploid relative, *Daysapyrun villosum*, but thus far no use has been made of this source of resistance because of the difficulty of transferring genes across such a taxonomically wide distance. No commercial wheat, barley, rye or triticale exists at the present time in the world with resistance to take-all, Rhizoctonia root rot, or Pythium root rot.

Methods available for biological control of fungal pathogens on plants have included bacterial strains of the species Pseudmonas having pathogen-specific activity. U.S. Pat. No. 4,456,684 describes Pseudomonas strains which suppress disease caused by take-all and other Gg fungi. Studies of the microbial antagonism involved in take-all decline, a natural biological control of take-all, defined as the spontaneous reduction in disease and the increase in yield with extended monoculture of Ggt-susceptible small grain crops such as wheat and barley, have focused on attempts to identify specific Ggt-antagonistic microorganisms and to transfer these organisms to soil to reproduce suppression. Many of the most effective strains produced the antibiotic 2,4-diacetylphloroglucinol (Phl) (C. Keel et al., *Applied and Environmental Microbiology* 62:552–563 (1996)). J. M. Raaijmakers et al. (*Applied and Environmental Microbiology* 63:881–887 (1997)) report that Phl-producing fluorescent Pseudomonus spp. were present on roots of wheat grown in three TAD soils from Washington State (USA). Although use of microbial biocontrol agents holds great promise as a practical means to control soilborne pathogens, all published or patented biocontrol agents for take-all have the disadvantages of performing inconsistently, being soil-specific, and being unable to duplicate the level of control consistently observed in a TAD soil.

U.S. Pat. No. 4,647,533 reports Pseudomonas strains which suppress diseases caused by Pythium. Strains of Pseudomonas bacteria inhibitory to either *Rhizoctonia solani* or *Pythium ultimum* on cotton have been reported. (See U.S. Pat. No. 5,348,742 to Howell et al.) Bacillus sp. L324-92 has been reported to simultaneously control *Gaeumannomyces graminis*, Rhizoctonia and Pythium species (Kim et al. *Phytopathology* 87:551–558 (1997)). However, no single Pseudomonas strain has been reported that is effective in controlling all three of these pathogens.

SUMMARY OF THE INVENTION

We have discovered transformed (transgenic) biocontrol agents for control of plant root diseases. In particular, the invention is directed to biologically pure cultures of transformed strains of fluorescent Pseudomonas species (spp.) which have a biosynthetic locus which encodes for the production of the antibiotic phenazine-1-carboxylic acid stably introduced into the genome, and which suppress (inhibit the incidence of or reduce the incidence or severity of) diseases caused by the soil-borne pathogen Rhizoctonia. Optionally, the strains suppress diseases caused by Pythium or diseases caused by *Gaeumannomyces graminis* (Gg) in addition to diseases caused by Rhizoctonia, or have the ability to control all three diseases.

The biocontrol agents of the invention are obtained by stably introducing the biosynthetic locus for phenazine-1-carboxylic acid into the genome of a strain of fluorescent Pseudomonas spp., hereinafter denoted as the parent strain, which contains a biosynthetic locus which encodes for the production of the antibiotic 2,4-diacetylphloroglucinol, has a unique genotype as shown by a characteristic unique Random Amplified Polymorphic DNA (RAPD) profile, and exhibits superior root colonizing ability as discussed below.

Screening of the transformed strains to select those having activity against diseases caused by Rhizoctonia is carried out in greenhouse bioassays. Optionally, to select transformed strains that are also effective against diseases caused by *Gaeumannomyces graminis* or Pythium, greenhouse assays can be carried out.

An optional step prior to the greenhouse screening bioassays is in vitro inhibition a Rhizoctonia isolate by a transformed strain.

Thus, the biocontrol agents of the invention provide biocontrol for diseases caused by Rhizoctonia and optionally diseases caused by Pythium and *Gaeumannomyces graminis*. We have found that exemplary transformed strains of the invention have the ability to suppress Rhizoctonia root rot at very low doses (as low as $10^2$ colony forming units (CFU) per seed). Further, we have found exemplary strains that additionally retain the ability of the parent strain to suppress other root diseases such as those caused by *Gaeumannomyces graminis* or Pythium. Thus, exemplary strains of the invention have activity against the three important plant root diseases—Rhizoctonia, Pythium, and *Gaeumannomyces graminis*.

A further aspect of the invention is application of the unique strains or compositions comprising the strains for biocontrol of plant root diseases. When used as a seed, soil, furrow treatment or drench, the unique strains of the invention have the ability to suppress diseases caused by Rhizoctonia under field conditions, and optionally may suppress diseases caused by Pythium or *Gaeumannomyces graminis*.

Additionally, the biocontrol agents of the present invention can be used to repare biocontrol mixtures which comprise at least one transgenic strain of the invention and include one or more other biocontrol strains, for example, additional transgenic strains of this invention; a parent strain of the invention strain, or other biocontrol strains.

In accordance with this discovery, it is an object of the invention to provide transgenic strains of fluorescent Pseudomonas spp. which have a biosynthetic locus which encodes for the production of the antibiotic phenazine-1-carboxylic acid stably introduced into the genome, and have biocontrol activity for control of plant root diseases, in particular, diseases caused by the soil-borne pathogen, Rhizoctonia, and optionally diseases caused by *Gaeumannomyces graminis* or Pythium.

It is also an object of the invention to provide methods of making the unique transgenic strains.

Another object of the invention is the provision of methods for biologically controlling root diseases in plants caused by Rhizoctonia, and optionally, other root diseases such as those caused by Pythium and *Gaeumannomyces graminis*.

It is a further object of the invention to provide agricultural compositions which comprise at least one biocontrol strain of the invention, which compositions are useful to control at least one plant root disease.

Other objects and advantages of the invention will become readily apparent from the ensuing description.

DETAILED DESCRIPTION OF THE INVENTION

Biocontrol Agents of the Invention. The biocontrol agents of the invention comprise at least one biologically pure strain of fluorescent Pseudomonas spp. which has the following identifying characteristics: the strain has a biosynthetic locus which encodes for the production of the antibiotic phenazine-1-carboxylic acid stably introduced into its genome; it retains the biosynthetic locus of the parent strain which encodes for the production of 2,4-diacetylphloroglucinol; and it suppresses diseases caused by the soil-borne pathogen Rhizoctonia. Optionally, the strain suppresses diseases caused by Pythium or the diseases caused by *Gaeumannomyces graminis* (Gg) in addition to diseases caused by Rhizoctonia, or has biocontrol activity (disease suppression ability) against all three root diseases.

Exemplary of the strains of the invention are *P. fluorescens* strains Z30-97; Z32-97; Z33-97; and Z34-97.

Figure 1:
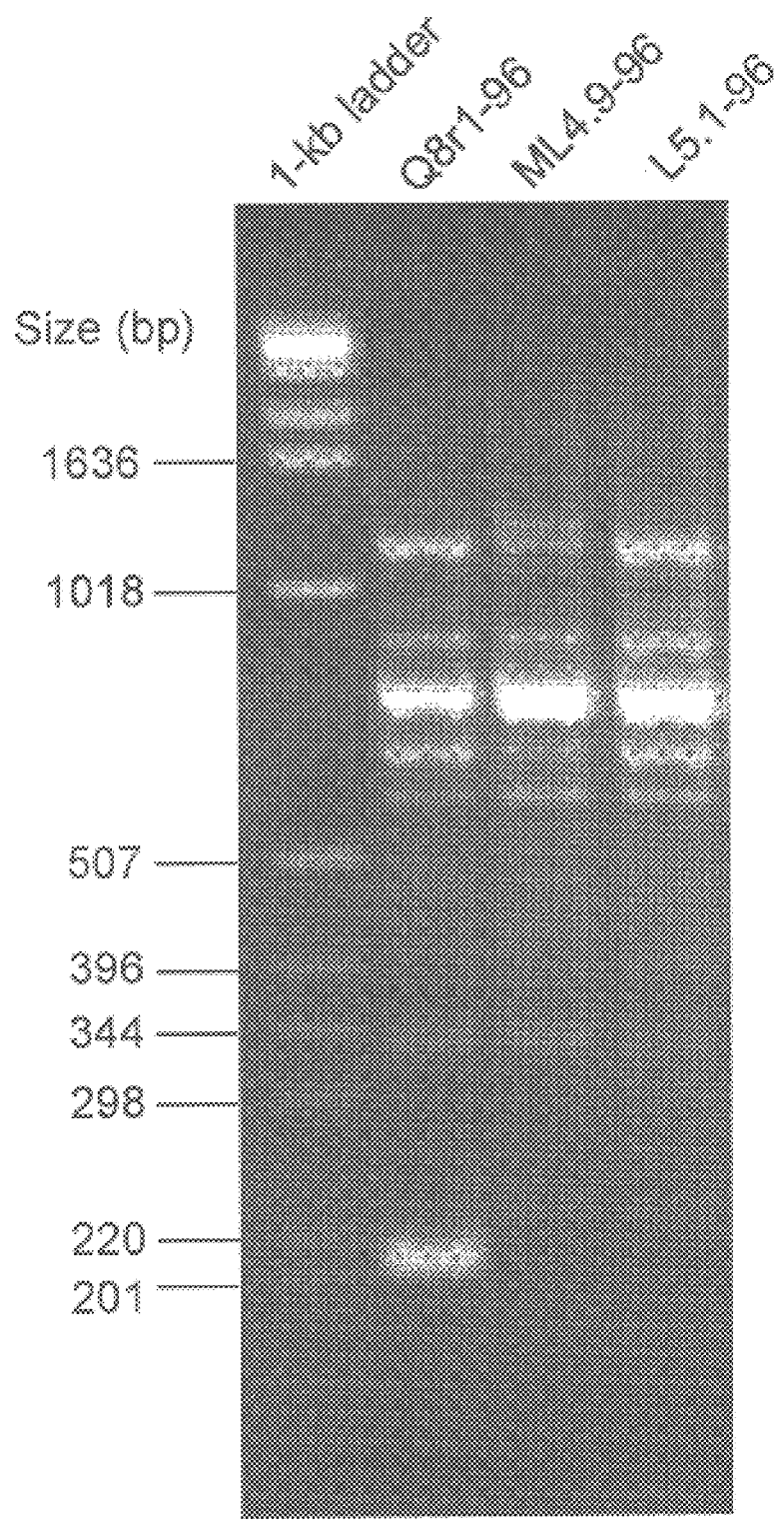
FIG. 1 is an image which shows the banding patterns (RAPD) of *P. fluorescens* strains Q8r1-96, ML4.9-96, and L5.1-96 which are exemplary parent strains useful to prepare the transgenic strains of the invention. Lane 1 shows a 1-kb ladder as a reference.

Characteristic Banding Pattern. Preferably, the transformed strain has the following additional identifying characteristic: it retains at least four of the characteristic bands of the banding pattern of the parent strain. The transformed strains of the invention share an identifying characteristic banding pattern with parent strains. This profile can be identified by Random Amplified Polymorphic DNA (RAPD) analysis using primer M13 as described in Examples 1 and 7, below. FIG. 1 shows the banding patterns (RAPD) of *P. fluorescens* Q8r1-96, ML4.9-96, and L5.1-96, which are exemplary parent strains of the invention. Lane 1 show a 1-kb ladder as a reference. As shown in FIG. 1, the bands shared by the exemplary parent strains are 330±20 bp; 600 bp±50 bp; 700±50 bp; 800 bp±50 bp; 900 bp±50 bp, and 1100 bp±60 bp. The band at 800 bp±50 bp is the most intense.

The transformed strains Z32-97; Z33-97, and Z34-97 share the following bands with their parent strain *P. fluorescens* Q8r1-96: 330±20 bp; 600 bp±50 bp; 700±50 bp; 800 bp±50 bp; 900 bp±50 bp, and 1100 bp±60 bp. The transformed strain Z30-97 shares the following bands with its parent strain Q8r1-96: 600 bp±50 bp; 700±50 bp; 800 bp±50 bp; 900 bp±50 bp.

For purposes of this invention, a transformed strain has the characteristic banding profile of the exemplary parent strain if it has bands at 600 bp±50 bp; 700±50 bp; 800 bp±50 bp; 900 bp±50 bp using the conditions described in Example 1 or 7, below. In a preferred embodiment, the transformed strain also has bands at 330±20 bp and 1100 bp±60 bp.

An alternative way to identify if a transformed strain has the characteristic banding pattern of the invention is to carry out a side-by-side comparison in an agarose gel using the exemplary parent strain *P. fluorescens* Q8r1-96, the actual parent strain, or an exemplary invention strain such as Z34-97 and the test strain and visually comparing the bands between about 600±50 and 900±50 base pairs. If the profile of the test strain matches the profile of the exemplary parent strain Q8r1-96, actual parent strain or exemplary invention strain in this region, then the test strain has the characteristic banding pattern encompassed by this invention.

Biocontrol activity. The biologically pure fluorescent Pseudomonas spp. strains of the invention have a biosynthetic locus which encodes for the production of the antibiotic phenazine-1-carboxylic acid stably inserted into the genome and have the ability to suppress (inhibit the incidence of or reduce the incidence or severity of) diseases caused by the soil-borne pathogen Rhizoctonia. Optionally, the strains suppress diseases caused by Pythium or diseases caused by *Gaeumannomyces graminis* in addition to diseases caused by Rhizoctonia, or have the ability to control all three diseases.

Tables 2, 3, and 4 in the Example 4, below, present data showing biocontrol activity. As shown in Table 2, transformed strains Z30-97, Z32-97, and Z34-97 at doses of $10^2$–$10^3$ CFU per seed reduced the percentage of wheat roots infected by Rhizoctonia solani AG8 as compared to the parental strain Q8r1-96 at a similar dose, *P. fluorescens* 2–79 (the source of the phenazine-1-carboxylic acid genes) and the two nontreated controls. The parental strain Q8r1-96 is equivalent to Z30-97 and Z32-97 in suppression of Rhizoctonia only when Q8r1-96 is applied at a larger dose. As shown in Table 3, in Example 4, below, strain Z34-97 at a dose of $10^2$ CFU/seed is as effective at suppressing Pythium as the parental strain Q8r1-96 at a dose of $10^3$ CFU/seed. As shown in Table 4, in Example 4, below, strain Z34-97 provides significant suppression of *Gaeumannomyces graminis* var. *tritici* (Ggt). As shown in Tables 14 in Example 4, below, Z34-97 is able to suppress all three root diseases.

Colonizing ability. The biologically pure transgenic strains have the ability to colonize plant seeds and roots. As shown in Table 5 in the Example 5, below, exemplary strains of the invention reached the same population density as the parent strain 66 hours and one week after planting treated seeds.

Application of Suppressive Transgenic Strains for Biocontrol of Plant Root Diseases. The transgenic microorganism strains of the invention are useful in controlling plant root diseases, in particular, diseases caused by the soil-borne pathogen, Rhizoctonia, and optionally, diseases caused by Pythium, and *Gaeumannomyces graminis*. The biocontrol agents of the invention find particular use in controlling root disease in small grains and turf grass. Examples of small grain crops include wheat, barley, rye, and triticale. Additionally, the strains may be used to control root disease on other food, fiber and ornamental plants, which are susceptible to root diseases caused by the soil-borne pathogens, Rhizoctonia, Pythium or *Gaeumannomyces graminis*. Such plants include asparagus, canola, corn, sugarbeet, tomatoes, potatoes, peas, rice, beans, soybeans, strawberries, zucchini, and cotton.

To achieve biocontrol of a target plant root disease or diseases in a particular plant, the plant is grown in the presence of an effective suppressive amount of one or more fluorescent Pseudomonas strains of the invention. An effective biocontrol amount is defined as that quantity of biocontrol agent which suppresses (inhibits the incidence or reduces the incidence or severity of) the target root disease or diseases relative to that occurring in an untreated control. This assumes that factors such as water, fertilizer, soil and air temperatures are not limiting to the growth of the target crop. An effective amount in a particular case can readily be determined by trial runs as known in the art.

Biocontrol is carried out by applying an effective amount of the biocontrol agent to a plant, to a seed of a plant or to the locus of the plant or seed. For example, the strain can be applied as a seed, soil or furrow treatment or as a drench to turf or soil. Fresh cells or freeze-dried cells may be used.

The strain may be incorporated into compositions suitable for application to plants where control of root disease is desired. It can be mixed with any agriculturally acceptable carrier or suitable agronomically acceptable carrier which does not interfere with the activity of the strain. Exemplary carriers are water, buffer, methylcellulose, ground peat or vermiculite. Where the strain is applied as a suspension or emulsion in a liquid carrier, the suspension or emulsion may optionally contain conventional additives such as surfactants or wetting agents as known in the art. The strain of the invention can also be formulated to include other biocontrol strains, including other strains of this invention, a parent strain, or strains known in the prior art.

Exemplary application procedures and exemplary effective amounts are described below. The amount that will be within an effective range in a particular instance can be determined by experimental tests.

For seed treatment of small grains or turf grass or other food, fiber or ornamental plants, bacteria are added to a suspension containing about 0.5–2.0% methylcellulose to minimize desiccation of the bacteria and promote adherence to the seed. The suspension is added to the seeds and mixed so that each seed is coated with about $10^2$ to $10^5$ CFU per seed. In general, the preferred amount is about $10^2$ to $10^4$ CFU per seed. Treated seeds are air dried.

For soil treatment, bacteria are suspended in water or buffer and applied to the soil to give about $10^2$ to $10^5$ CFU per gram of soil. For turf, the bacteria are suspended in water or buffer and applied to the grass as a drench containing about $10^2$ to $10^5$ CFU per ml.

For direct treatment of roots, roots are dipped into a bacterial suspension of about $10^2$ to $10^5$ CFU per ml of suspension.

Where the carrier is a solid, e.g., peat or vermiculite, a typical formulation is about $10^6$ to $10^9$ CFU per gram of carrier. Where the carrier is a liquid, a typical formulation is about $10^8$ to $10^{10}$ CFU per ml of carrier. For a freeze-dried formulation, a typical amount is about $10^{10}$ to $10^{11}$ CFU per gram formulation. Freeze dried formulations may contain additives as known in the art.

Preparation of the Strains of the Invention. Strains of the invention are obtained by recombinant DNA technology wherein the biosynthetic locus for phenazine-1-carboxylic acid is stably introduced into the genome of a parent strain of fluorescent Pseudomonas having the characteristics described in detail below.

The genetic locus for biosynthesis of phenazine-1-carboxylic acid from a bacterial strain, such as a fluorescent Pseudomonas, is modified by inserting the phenazine biosynthetic genes behind a promotor, such as tac. This construction then is cloned into a plasmid such as pUT which contains a mini-Tn5 with cloning sites such as SfiI or NotI, and which has the ability to mediate stable insertion of the phenazine biosynthetic genes into the recipient fluorescent Pseudomonas. The plasmid with the phenazine biosynthetic locus and promotor is carried in a strain such as *Escherichia coli* S17-1(λ.pir). The phenazine biosynthetic genes are stably inserted into the recipient Pseudomonas strain by mating with the *E. coli* strain with the recipient Pseudomonas strain (bacterial conjugation). After matings, cultures are suspended in buffer and planted onto KMB plus kanamycin. Strains which are fluorescent and kanamycin resistant are putative transformed (transgenic) strains.

As discussed in Example 2, below, a transposable version of the genetic locus for biosynthesis of phenazine-1-carboxylic acid was constructed using phenazine biosynthetic genes from *Pseudomonas fluorescens* strain 2-79 (NRRL B-15132). The phenazine biosynthetic (phz) locus is localized in *P. fluorescens* 2-79 within a 8,505-bp BglII-XbaI DNA fragment, and consists of 9 genes designated as phzABCDEFG, phzI and phzR. The complete sequence of the phz locus from *P. fluorescens* 2-79 is listed in the GenBank computer database under the accession number L48616.

The phzABCDEFG genes are organized in a single operon and are responsible for phenazine-1carboxylic acid (PCA) production in *P. fluorescens* 2-79. Products of the phzC, phzD, and phzE genes share similarities with enzymes of shikimic acid and chorismic acid metabolism and, together with PhzF, are absolutely necessary for PCA production. PhzG is similar to pyridoxamine-5'-phosphate oxidases and probably is a source of cofactor for PCA-synthesizing enzyme(s). Products of the phzA and phzB genes are highly homologous to each other and may be involved in stabilization of a putative PCA-synthesizing multienzyme complex. The phzABCDEFG genes are localized within a 6.8-kb BglII-XbaI fragment from the phenazine biosynthesis locus of strain 2-79. This DNA fragment was placed under control of the tac promoter, and then cloned in the delivery plasmid described below. The resulting plasmid was used to generate stable chromosomal inserts in fluorescent Pseudomonas spp. that are naturally unable to produce phenazine compounds.

To construct genetically engineered bacterial strains the system based on the transposon features of Tn5 and the delivery properties of plasmid pUT was used (V. de Lorenzo, M. Herrero, U. Jakubzik and K. N. Timmis, *Journal of Bacteriology* 172:6568–6572 (1990)). pUT has a π protein-dependent origin of replication of plasmid R6K and is only maintained in π protein-producing bacteria, e.g., a specially engineered *Escherichia coli* S17-1(λpir) strain. pUT also carries the origin of transfer oriT of plasmid RP4, which results in its efficient conjugal transfer to recipient Pseudomonas strains from donor *E. coli* strains expressing RP4-conjugative functions. Finally, pUT carries a tnp gene of $IS50_R$ that encodes the transposase needed for transposition of the mini-Tn5 elements. With the delivery system described above, phenazine biosynthetic genes are inserted into the chromosome of target Pseudomonas strains, where they are maintained at a low, often natural copy number, and should be, at least theoretically, as stable as other chromosomal genes.

After matings, cultures are suspended in buffer and plated onto KMB plus kanamycin. Strains which are fluorescent and kanamycin resistant are putative transformed strains. The selected individual colonies are picked, streaked, and restreaked until the strain is stable and pure, that is, it is a biologically pure culture. The strain can be stored in glycerol at −80° C. to keep it stable.

Screening in the Greenhouse. Screening of the transformed strains to select those having activity against diseases caused by Rhizoctonia, such as Rhizoctonia root rot of wheat, is carried out in greenhouse bioassays. Soil is infested with inoculum of Rhizoctonia and placed in plastic tubes as described in the Example 4, below. Seed of a susceptible crop such as wheat is treated with he transformed strain and sown in the soil. Optionally, to select transformed trains that are also effective against diseases caused by *Gaeumannomyces graminis* (Gg) or Pythium, greenhouse bioassays are conducted utilizing Gg or Pythiwn spp. as the inoculum, respectively.

Optional Screening In Vitro. An optional step prior to the greenhouse screening is in vitro inhibition of a Rhizoctonia isolate by a transformed strain. The assay involves pairing a transformed strain with the pathogen on an agar plate and measuring the size of the zone of inhibition. As discussed in Example 3, below, exemplary biologically pure transgenic strains showed greater in vitro inhibition of *Gaeumannomyces graminis* var. *tritici, Rhizoctonia solani* AG8 and *Pythimn irregulare* than parent strain *P. fluorescens* Q8r1-96. As shown in Table 1 in Example 3, below, the zones of inhibition of the transgenic strains are significantly greater than that of Q8r1-96. Optionally, the strains suppress diseases caused by Pythium or diseases caused by *Gaeumannomyces graminis* (Gg) in addition to diseases caused by Rhizoctonia, or have the ability to control all three diseases.

Using our method we obtained biologically pure cultures of *P. fluorescens* stains Z30-97; Z32-97; Z33-97, and Z34-97, which are exemplary of the strains of the invention. These strains were obtained by transformation of parent strain *P. fluorescens* Q8r1-96 to introduce the biosynthetic locus for phenazine-1-carboxylic acid stably into the genome. This is discussed in detail, below, in Example 2. Parent strain Q8r1-96 normally produces the antibiotic 2,4-diacetylphloroglucinol (Phl) and introduction of the PCA biosynthetic genes conferred on the transformed strains the ability to produce phenazine-1-carboxylic acid in addition to Phl.

As shown in Example 4, below, the addition of the phenazine-larboxylic acid biosynthetic genes resulted in transformed strains that are significantly better at suppressing Rhizoctonia root rot than the parent strain Q8r1-96 or strain 2-79, the strain which is the source of the phenazine-1-carboxylic acid biosynthetic locus. As shown in the Example, strain Z34-97 was effective at suppression of Rhizoctonia at a dose of $10^2$ to $10^3$ which is a 100–1000 fold lower dose than the dose needed for suppression by other Rhizoctonia suppressive strains, including *P. fluorescens* Q8r1-96 and Bacillus sp. L324-92.

Strain Characteristics. The exemplary parent strain Q8r1-96 shows physiological traits and substrate utilization patterns typical of *P. fluorescens* as described in Bergey's Manual (see Table 6, below). Strain Q8r1-96 also produces the antibiotic 2,4-diacetylphloroglucinol. Transformed strains of the invention exemplified by Z34-97 share the traits of the exemplary parent strain except that the transformed strains produce phenazine-1-carboxylic acid in addition to 2,4-diacetylphloroglucinol.

Statement of Deposit. Biologically pure cultures of *P. fluorescens* strains Z32-97, Z33-97, and Z34-97 were deposited Dec. 11, 1997 and a biological pure culture of *P. fluorescens* strain Z30-97 was deposited Dec. 15, 1997 in the Agricultural Research Culture Collection (NRRL), 1815 North University Street, Peoria, Ill. 61604, and have been assigned the accession numbers NRRL B-21905, NRRL B-21906, NRRL B-21907, and NRRL B-21908, respectively. All strains were deposited under terms of the Budapest Treaty. Strains having the identifying characteristics of NRRL B-21905, NRRL B-21906, NRRL B-21907 or NRRL B-21908 are encompassed by this invention. For the purpose of this invention, any isolate having the identifying characteristics of strains NRRL B-21905, NRRL B-21906, NRRL B-21907 or NRRL B-21908, including subcultures and variants thereof which contain a biosynthetic locus which encodes for the production of the antibiotic phenazine-1-carboxylic acid stably introduced into the genome, and which suppress diseases caused by the soil-borne pathogen Rhizoctonia, and retains the locus of 2,4-diacetylphloroglucinol of the parent strain are included. In a preferred embodiment, the isolate also retains four bands of the genetic profile of the parent strain, as discussed in detail, above. The term variants is defined herein to include transformants and mutants which having the aforenamed characteristics.

Growth of the Strains of the Invention. The fluorescent Pseudomonas spp. strains of the invention can be grown on any suitable solid or liquid bacteriological medium. An exemplary medium is King's medium B. Growth of the strains are effected under aerobic conditions at any temperature satisfactory for growth of the organism, i.e., from about 15° C. to 30° C.; the preferred temperature range is about 24° C. to 28° C. The pH of the nutrient medium is preferably about neutral, i.e., pH 6.7–7.2.

Maintenance of Stock Cultures. Each strain is maintained to keep it stable, such as by storing in glycerol at −80° C.

Parent Strains for Preparation of the Transgenic Strains of the Invention. Parent strains useful for preparation of the transgenic strains of the invention are those which have the following characteristics: the strain contains a biosynthetic locus which encodes for the production of 2,4-diacetylphloroglucinol and it has a unique genotype as shown by a characteristic banding pattern described in detail, below, and in FIG. 1. This profile can be identified by RAPD-analysis with primer M13 as described in Example 1, below. Exemplary parent strains are *P. fluorescens* strains Q8r1-96, L5.1-96, and ML4.9-96. Biologically pure cultures of strains Q8r1-96, L5.1-96, and ML4.9-96 were deposited Jul. 8, 1997 under terms of the Budapest Treaty in the Agricultural Research Culture Collection (NRRL), 1815 North University Street, Peoria, Ill. 61604, and have been assigned the accession numbers NRRL B-21806, NRRL B-21807, and NRRL B-21808, respectively.

FIG. 1 shows the banding patterns (RAPD) of parent *P. fluorescens* strains Q8r1-96, ML4.9-96, and L5.1-96. Lane 1 shows a 1-kb ladder as a reference. As shown in FIG. 1, the bands shared by the strains are: 330±20 bp; 600 bp±50 bp; 700±50 bp; 800 bp±50 bp; 900 bp±50 bp, and 1100 bp±60 bp. The band at 800 bp±50 bp is the most intense.

For purposes of this invention, a parent strain has the characteristic banding profile if it has bands at 600 bp±50 bp; 700±50 bp; 800 bp±50 bp; 900 bp±50 bp using the conditions described in Example 1, below. In a preferred embodiment, the parent strain also has bands at 330±20 bp and 1100 bp±60 bp.

An alternative way to identify if a parent strain has the characteristic banding pattern is to carry out a side-by-side comparison in an agarose gel using *P. fluorescens* strain Q8r1-96 and the test strain and visually comparing the bands between about 600±50 and 900±50 base pairs. If the profile of the test strain matches the profile of strain Q8r1-96 in this region, then the test strain has the characteristic banding pattern, and optionally, in addition, it suppresses diseases caused by Gg in field-grown small grain crops or turf grass, and it exhibits rootcolonizing ability which is characterized by both higher population density and extended colonizing activity compared to known Gg-suppressive strains.

Biocontrol Activity of Parent Strain. The biologically pure fluorescent Pseudomonas spp. parent strains preferably have the ability to suppress (inhibit the incidence of or reduce the incidence or severity of) diseases caused by Gg, such as take-all, in small grain crops or turf grass. For example, exemplary parent strain Q8r1-96 reduced the percentage of wheat plants infected with take-all in the field by 20% compared to nontreated seed (control). Also, strain Q8r1-96 was shown to be nearly twice as effective at reducing take-all as *P. fluorescens* strain Q2-87 (a known suppressive Phl-producing strain) after 9 cycles of cropping wheat. As discussed below, Q8r1-96 duplicated the biocontrol of TAD soil.

As shown in the Tables 2–4, below, the exemplary parent strain Q8r1-96 is able to provide biological control of three important root disease of wheat and other small grains, including tall, caused by *Gaeumannomyces graminis* var. *tritici*, Rhizoctonia root rot, caused by *Rhizoctonia solani* AG8, and Pythium root rot, cause by a complex of Pythium spp. including *Pythium irregulare*.

Colonizing ability of parent strain. The biologically pure fluorescent Pseudomonas spp. parent strains show a unique colonizing ability which is characterized by both (a) higher population density on the roots and (b) extended colonizing activity compared to known suppressive strains. That is, the parent strains have the ability to both colonize and persist on the roots of small grains. Preferably, parent strains have the ability to colonize roots at a population density averaging at least about $10^5$ colony forming units (CFU)/gram of root, including the associated rhizosphere soil, for at least 7 successive growth cycles. Colonization of wheat (cv Penawawa) roots by Q8r1-96 was monitored during 9 cycles of wheat in Quincy virgin soil. By cycle 5, the population density of Q8r 1-96 was nearly 1000-fold greater than that of *P. fluorescens* strains Q2-87 and M1-96 (strains not in accordance with the invention). Q8r1-96 also showed significantly greater population densities in the Land and Moses lake virgin soils. For these experiments, each cycle consisted of wheat grown in soil for 3 weeks, and the plants were harvested and bacterial populations on the roots determined by dilution plating. The soil and associated root system was decanted into a plastic bag, and shaken to aerate and mix the soil. One week after harvest each soil was returned to the same pot and again sown to wheat. Thus, each cycle between planting lasted 4 weeks.

Duplication of Biocontrol of TAD Soil. A parent strain of the invention is preferably further characterized by having the ability to suppress diseases caused by Gg in small grain crops that is equivalent to a level of biocontrol obtained when the small grain crop is grown in a soil in a state of take-all decline (TAD). That is, the strain has the ability to duplicate the level of biocontrol obtained in a take-all decline soil. For example, the exemplary parent strain Q8r1-96 applied at a dose of $10^4$ colony forming units (CFU)/seed and then sown in Quincy virgin (conducive) soil was as effective at suppressing take-all as the Quincy TAD soil. In addition, Qr81-96 was as effective in Lind virgin (conducive) soil as Quincy TAD soil added at 10%w/w into the Lind virgin soil. This duplication of suppression of take-all equivalent to natural take-all decline is unprecedented.

Method of Obtaining Parent Strains.

Step 1. Successive growth cycles to enrich for Phl producers.

In this step, a small grain crop or turf grass is cultivated in successive growth cycles in natural take-all suppressive soil to enrich for Phl-producing fluorescent Pseudomonas spp. as follows: (a) growing seeds of a small grain crop or growing turf grass in a soil in a state of take-all decline (CAD soil) in the greenhouse for at least 3 weeks and under conditions effective to support growth of said small grain crop or turf grass to obtain seedlings; (b) collecting the soil and roots of the small grain crop or turf grass seedlings grown in the soil and mixing them together; and (c) repeating steps (a) through (b) for at least a total of 4 successive cycles, wherein the mixture of step (b) is used to grow the seeds in the succeeding cycle.

Step 2. Isolation of fluorescent Pseudomonas spp. from roots cycled in TAD soils.

In this step, strains of potentially-suppressive fluorescent Pseudomonas bacteria are isolated from the roots and associated rhizosphere soil of the small grain crop or turf grass successively cultivated in step (1) by growing the strains on a Pseudomonas-selective medium for a time and under conditions effective for growth of Pseudomonads and selecting strains which grow on the medium.

Step 3. Colony hybridization with specific probes to detect Phl producers. In this step, strains isolated in step 2 are screened to select a strain which contains a biosynthetic locus which encodes for the production of 2,4-diacetylphloroglucinol (Phl) by hybridizing a colony of the strains with a 2,4-diacetylphloroglucinol-specific probe and selecting strains that hybridize to the probe. The selected individual colonies are picked, streaked, and restreaked until the strain is stable and pure, that is, it is a biologically pure culture. The strain can be stored in glycerol at $-80°$ C. to keep it stable.

Step 3a (optional). Confirmation of Phl-producers by PCR.

In this optional step, confirmation of Phl producing strains is carried out using primers which amplify sequences within the Phl biosynthetic locus, and those strains that give a positive PCR reaction are selected.

Step 4. RAPD analysis to identify Phl-producers with the definitive banding pattern.

In this step, Random Amplified Polymorphic DNA analysis is carried out using primer M13 (Sequence:

GGTGGTCAAG) (see Keel et al., supra). Primer M13 is available commercially from Operon Technologies Inc., Alameda, Calif. Strains which have bands at 600 bp±50 bp; 700±50 bp; 800 bp±50 bp; 900 bp±50 bp are selected. It is preferred that the strains also have bands at 330±20 bp and 1100 bp±60 bp.

Biologically pure cultures of *P. fluorescens* strains Q8r1-96, L5.1-96, and ML4.9-96 which are exemplary of parent strains, were obtained by the above method.

Growth of the parent strains and maintenance of stock cultures of the parent strains are carried out as described above with reference to the transgenic strains of this invention.

EXAMPLES

The following examples are intended only to further illustrate the invention and are not intended to limit the scope of the invention which is defined by the claims.

Example 1

The following example describes the selection of parent fluorescent Pseudomonas spp.

Overview. *Pseudomonas fluorescens* strains Q8r1-96, L5.1-96, and ML4.9-96 were isolated in 1996 from roots of wheat grown in soils collected from agricultural fields near, respectively, Quincy, Lind, and Moses Lake, Washington (USA) that are in the state of take-all decline (TAD). Q8r1-96 was isolated from roots of wheat grown in Quincy TAD soil for 8 successive cycles of 3 weeks each; L5.1-96 from roots of wheat grown in Lind TAD soil for 5 successive cycles of 3 weeks each; ML4.9-96 from roots of wheat grown in Moses Lake TAD soil for 4 successive cycles of 3 weeks each.

The following is a detailed description of the soils and the isolation and characterization techniques.

Soils. The three different soils were obtained from agricultural fields in the state of TAD near Quincy, Lind, and Moses Lake, Wash. (USA). All three soils are suppressive to take-all of wheat. In 1995, the Lind TAD field had been cropped continuously to wheat for 28 years. In 1980, the TAD fields at Quincy and Moses Lake had been cropped continuously to wheat for 22 years; between 1980 and 1995 other crops besides wheat also were grown. The soils were collected in March 1995 from the upper 30 cm of the soil profile, air-dried for 1 week and passed through a 0.5-cm mesh screen prior to use. Their physical and chemical properties were determined by the Analytical Sciences Laboratory, University of Idaho.

Step 1: Successive growth cycles of wheat to enrich for Phl producers.

Twelve wheat seeds were sown in square PVC pots (8 cm high, 7.5 cm wide) containing 200 g of sieved natural soil (Quincy, Lind, or Moses Lake TAD soil) and 50 ml of water supplemented with metalaxyl (Novartis, Greensboro, N.C.) at 2.5 mg/ml active ingredient to control Pythium root. Pseudomonads are not affected by this fungicide. A 1-cm layer of soil was spread on top of the seeds. Plants were grown in a controlled-environment chamber at 16° C. with a 12-hour photoperiod. Pots received 50 ml of dilute (2:3, vol/vol) Hoaglund's solution (macro-elements only) twice a week. After 3 to 4 weeks of growth, the shoots of the plants were excised at the soil surface, and the soil and associated root system was decanted into a plastic bag and shaken vigorously to aerate and mix. This 'cultivated' soil was stored for 1 week at 15° C., returned to the same pot, and then replanted with twelve wheat seeds. This process of plant growth and harvesting was repeated for at least four and up to eight successive cycles, at which time four randomly selected plants were harvested from each replicate and root samples were prepared to determine the population size of antibiotic-producing fluorescent Pseudononas spp. For each soil, four replicates were used.

Step 2: Isolation of fluorescent Pseudomonas spp. from roots of wheat cycled in TAD soils.

Four randomly selected plants grown in step 1 were harvested from each replicate, and loosely adhering soil was removed from the roots by gently shaking. 1.0 g of roots and associated rhizosphere soil was suspended in 5.0 ml of sterile ater and shaken vigorously for 1 minute on a Vortex mixer. The samples were subsequently sonicated in a ultrasonic cleaner for 1 minute, and then serial dilutions of the root wash were plated onto King's medium B [KMB] agar (Proteose peptone, 20 g; glycerol, 10 ml; $K_2HPO_4$, 1.5 g; $MgSO_4$, 1.5 g; agar, 15 g; $H_2O$, 1000 ml) supplemented with cycloheximide (100 µg/ml), chloramphenicol (13 µg/ml) and ampicillin (40 µg/ml) [$KMB^+$]. Plates were incubated at 25° C., and colonies were enumerated after 48 hours. Colonies of fluorescent Pseudomonas spp. were differentiated from non-fluorescent colonies under UV light (wavelength 366 nm).

Step 3: Colony hybridization with specific probes to detect Phl producers.

The number of fluorescent Pseudomonas spp. that harbor the genes for Phl was determined by colony hybridization. Transfer of bacterial colonies to Hybond-$N^+$ nylon membranes (Amersham) was performed by standard methods. After air drying, the membranes were baked for 1 hour at 80° C. in a vacuum oven. To remove bacterial cell debris, membranes were washed for 1.5 hours at 42° C. in a solution containing 2×SSPE (20 mM $NaH_2PO_4$ [pH 7.4], 0.36 M NaCl, 2 mM EDTA), 0.1% sodium dodecyl sulfate (SDS) and pronase (100 µg/ml) and washed again for 1 hour at 56° C. in 2×SSPE and 0.1% SDS. Hybridizations were performed by standard methods. High stringency conditions consisted of prehybridization for 1.5 hour at 65° C., hybridization for 12 hours at 65° C., membrane washing twice each for 5 minutes with 2×SSC and 0.1% SDS at room temperature, and membrane washing twice each for 30 minutes with 0.1×SSC and 0.1% SDS at 65° C.

Probes were generated from sequences within the biosynthetic locus for 2,4-iacetylphloroglucinol (GenBank accession no. U41818). The probe was developed from sequences within phlD of Q2-87 by random primed labeling of PCR fragments using the nonradioactive DIG system (Boehringer Mannheim). The hybridized probes were immunodetected with anti-digoxigenin-AP-Fab fragments and were visualiz with the colorometric substrates nitroblue tetrazolium salt and 5-bromo-4-chloro-3-indolylphosphate, according to protocols provided by the supplier.

In order to isolate Phl producers, the signals on the membrane were aligned with the colonies on the agar plate. Each individual colony which gave a signal on the membrane was picked, streaked, and restreaked until the strain was stable and pure, that is, it is a biologically pure culture. Each strain was stored in glycerol at −80° C. to keep it stable.

Step 3a (optional): Confirmation of Phl-producers by PCR. This optional step allows false positives from the colony hybridization to be eliminated from analysis.

Heat-lysed bacterial suspensions used in PCR analysis were prepared from cultures grown on KMB for 48 hours at 25° C. Two bacterial colonies (2 mm diam) were suspended in 100 μl lysis solution (0.05 M NaOH, 0.25% SDS) and incubated for 15 min at 100° C. The suspension was centrifuged for 1 min at 12,000 rpm and diluted 50-fold in sterile distilled water. Five μl of the diluted suspension were used in each reaction.

Primers and PCR analysis. The oligonucleotide primers used in the PCR were developed from sequences within the biosynthetic locus for 2,4-diacetyl-phloroglucinol (Phl) of *P. fluorescens* Q2-87 (GenBank accession no. U41818). Primers were synthesized by Operon Techn. Inc. (Alameda, Calif.). Primers Phl2a (Sequence ID NO:2: GAGGACGTCGAAGACCACCA) and Phl2b (Sequence SEQ ID NO:3: ACCGCAGCATCGTGTATGAG) were developed from sequences within phlD, which predicts a protein of 349 amino acids that is homologous to chalcone synthase from plants.

PCR amplification was carried out in a 25-μl reaction mixture, which contained 5 μl of a diluted heat-lysed cell suspension, 1×GeneAmp PCR buffer (Perkin Elmer Corp., Norwalk, Conn.), 200 μM each of dATP, dTTP, dGTP, and dCTP (Perkin Elmer), 20 pmole of each primer, and 2.0 U of AmpliTaq DNA polymerase (Perkin Elmer). Each mixture was covered with one drop of mineral oil. Amplifications were performed in a Perkin Elmer Thermal Cycler 480. The PCR program consisted of an initial denaturation at 94° C. for 2 min followed by 30 cycles of 94° C. for 60 s, 67° C. for 45 s, and 72° C. for 60 s. Samples (9 μl) the PCR products were separated on a 1.2% agarose gel in 1×TBE buffer (90 mM Tris-borate, 2 mM EDTA (pH 8.3)) at 75 V for 3 hours. The gel was stained with ethidium bromide for 30 minutes, and the PCR products were visualized using a UV transilluminator.

Step 4: RAPD analysis to identify Phl-producers with the definitive banding pattern. RAPD-analysis (Random Amplified Polymorphic DNA) with primer M13 was performed for clustering the different Phl-producing fluorescent Pseudomonas strains isolated from roots of wheat grown in Quincy, Lind and Moses Lake TAD soil.

Amplification of the DNA was carried out in a 25-μl reaction mixture, which contained 5 μl of a diluted heat-lysed cell suspension, 1×GeneAmp PCR buffer (Perkin Elmer Corp., Norwalk, Conn.), 200 μM each of dATP, dTTP, dGTP, and dCTP (Perkin Elmer), 80 pmole of primer M13, and 2.0 U of AmpliTaq DNA polymerase (Perkin Elmer). Each mixture was covered with one drop of mineral oil. Amplifications were performed in a Perkin Elmer Thermal Cycler 480. The PCR program consisted of an initial denaturation at 94° C. for 1 min 30 sec followed by 2 cycles of 94° C. for 30 sec, 36° C. for 30 sec, 72° C. for 2 min, followed by 40 cycles of 94° C. for 20 sec, 36° C. for 15 sec, 45° C. for 15 sec, 72° C. for 1 min 30 sec, followed by 1 cycle of 72° C. for 10 min. Samples (9 μl) of the PCR products were separated on a 2.5% agarose gel in 1×TBE buffer (90 mM Tris-borate, 2 mM EDTA (pH 8.3)) at 75 V for 5 hours. The gel was stained with ethidium bromide for 60 minutes, and the PCR products were visualized using a UV transilluminator.

The biologically pure fluorescent Pseudomonas parent strains show a unique banding pattern as demonstrated by RAPD-analysis with primer M13. FIG. 1 shows the banding patterns (RAPD) of *P. fluorescens* strains Q8r1-96, ML4.9-96, and 15.1-96. Lane 1 shows a 1-kb ladder as a reference. As shown in FIG. 1, the bands shared by the parent strains are: 330±20 bp; 600 bp±50 bp; 700±50 bp; 800 bp±50 bp; 900 bp±50 bp, and 1100 bp±60 bp.

Example 2

The following example describes construction of exemplary transgenic phenazine-producing strains of fluorescent pseudomonads. In all experiments listed below, standard methods were used for plasmid DNA isolation, restriction enzyme digestion, agarose gel electrophoresis, ligation, and transformation (Ausubel, F. M., R. Brent, R. E. Kingston, D. D. Moore, J. G. Seidman, J. A. Smith, and K. Struhl (ed.), 1995. *Short Protocols in Molecular Biology*. J. Wiley and Sons, N.Y.). All enzymes (including restriction endonucleases, T4 DNA ligase, Klenow fragment of DNA polymerase I) and reagents that are necessary for conducting experiments described below, are commercially available from Life Technologies, Gaithersburg, Md. The QIAEX II Gel Extraction Kit available from QIAGEN Inc., Chatworth, Calif. was used for DNA extraction from agarose gels. *Escherichia coli* strain JM109 that was used for all DNA cloning experiments is commercially available from Promega Corporation, Madison, Wis. All bacterial strains were routinely propagated on LB medium (Bacto tryptone (Difco Laboratories, Detroit, Mich.), 10 g; Bacto yeast extract (Difco Laboratories, Detroit, Mich.), 5 g; NaCl, 5 g; $H_2O$, 1000 ml).

Step 1. Cloning of phz genes under control of tac promoter.

The 6.8-kb BglII-XbaI DNA fragment containing phzA,-B,-C,-D,-E,-F and -G genes from *P. fluorescens* 2-79 was inserted into the BamHI and XbaI cloning sites of the pALTER-Ex1 cloning vector, which contains a versatile polylinker combined with a strong tac promoter for in ivo and in vitro expression of cloned genes. The pALTER-Ex1 cloning vector is available commercially from Promega Corporation, Madison, Wis. After ligation the DNA sample was transformed into competent cells of *E. coli* JM109, and transformants were selected on LB agar amended with 12 μg/ml of tetracycline. Several individual colonies were grown in LB broth with tetracycline and used to purify plasmid DNA. The insertion of phz biosynthetic locus was confirmed through digests with restriction endonucleases.

Step 2. Construction of a transposable copy of the phenazine biosynthetic locus.

The DNA of pALTER-Ex1 containing phz genes was digested with ScaI, XbaI and HindIII restriction endonucleases, which generated 6.8-kb, 4.3-kb, and 1.4-kb DNA fragments. The 6.8-kb HindIII-XbaI DNA fragment containing phz genes linked to the tac promoter (FIG. 2) was separated from the other fragments by preparative gel electrophoresis, purified from the agarose gel, and blunt-ended with Klenow fragment of DNA polymerase I. This fragment was ligated with DNA of pUC18Sfi cloning vector (M. Herrero, V. de Lorenzo, K. Timmis, *Journal of Bacteriology* 172:6557–6567(1990)),which was previously cut with EcoRI restriction endonuclease and treated with Klenow fragment of DNA polymerase I. The ligation mixture was transformed into *E. coli* JM109 and transformants with the inserted phz locus were screened by their white colony color on LB agar supplemented with 40 μg/ml of 5-bromo-4-chloro-3-indolyl-β-D-galactopyranoside (X-gal) and 80 μg/ml of ampicillin. Samples of plasmid DNA from transformants with white colonies were screened for the presence of phz genes as described above.

Figure 2:
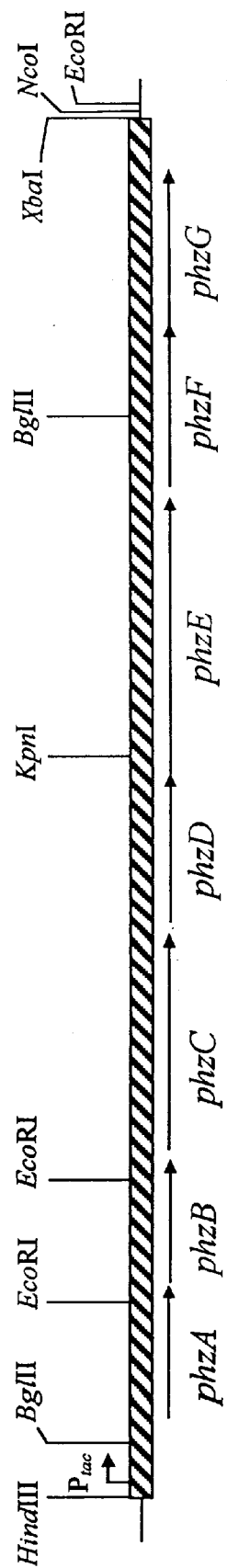
FIG. 2 shows the physical map of the phenazine biosynthetic locus linked to the tac promoter. Arrows indicate genes encoding phenazine biosynthesis enzymes and the direction of their transcription. The symbol $P_{tac}$ represents the position and orientation of the tac promoter.
Figure 3:
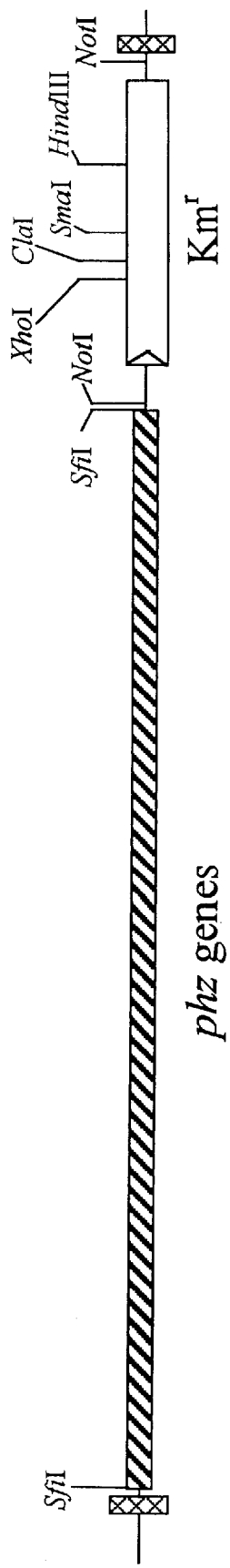
FIG. 3 shows the physical map of pUTKm::phz plasmid. Slanted lines indicate phenazine biosynthetic genes. Position and direction of the transcription of the determinant for kanamycin resistance is shown as an open box. Small boxes with "X"s indicate position of the Tn5 19-bp terminal ends.

The hybrid pUC18Sfi plasmid containing the phz locus was digested with SfiI restriction endonuclease, and ligated with the pUTKm plasmid (see Herrero et al.) opened with SfiI. The competent cells of *E. coli* S17-1(λpir) were transformed with the ligation mixture and transformants were selected on LB supplemented with kanamycin and ampicillin, each at 100 μg/ml. Plasmid DNA from several individual colonies was purified and screened for the presence of phz genes by cleavage with restriction endonucleases EcoRI and HindIII. The genetic map of the resulting plasmid pUTKm::phz is shown in FIG. 2. *E. coli* S17-1 (λpir) harboring pUTKm::phz was used as the donor for conjugation with Pseudomonas spp.

Step.3. Conjugation between *E. coli* S17-1(λpir) and Pseudomonas spp.

Plasmid pUTKm::phz was mobilized from *E. coli* S17-1 (λpir) to *Pseudomonas fluorescens* Q8r1-96 using a mating technique described by Herrero et al. The donor strain *E. coli* S17-1(λpir) harboring pUTKm::phz was grown overnight with shaking at 37° C. in 10 ml of LB broth supplemented with 100 μg/ml of both ampicillin and kanamycin. The rifampicin-resistant Q8r1-96 recipient strain was separately grown overnight in 10 ml of LB broth without antibiotics. The cultures of donor and recipient strains were separately centrifuged at 6,000 rpm for 5 min and cells were suspended in 1 ml of fresh LB broth. 30 μl of the cell suspension of donor *E. coli* S17-1(λpir) strain was spotted on a piece (2×2 cm) of nitrocellulose membrane placed on an LB plate, and then 20 μl of the cell suspension of a recipient strain was spotted over donor. Pure nitrocellulose membrane (0.45 micron) is commercially available from Bio-Rad Laboratories, Hercules, Calif. The plates with membranes were incubated at 27° C. overnight, and then cells from the membranes were suspended in 1 ml of sterile water. Cells were pelleted by centrifugation at 6,000 rpm for 5 min and then suspended in 1 ml of sterile water. The suspension of cells was diluted 10-fold, and 100 μl was plated on M9 minimal medium $Na_2HPO_4 \times 7H_2O$, 21 g; $KH_2PO_4$, 3 g; NaCl, 0.5 g; $NH_4Cl$, 1.0 g; 1M $CaCl_2$, 0.1 ml; 1M $MgSO_4$, 2 ml; 20% glucose, 20 ml; $H_2O$ to 1000 ml), supplemented with 100 μg/ml of kanamycin and incubated at 27° C. for 3 days. Several colonies of the Q8r1-96 recipient strain that had grown on M9-kanamycin plates were transferred to King's medium B plates (Proteose peptone (Difco Laboratories, Detroit, Mich.), 20 g; glycerol, 10 ml; $K_2HPO_4$, 1.5 g; $MgSO_4$, 1.5 g; Bacto agar (Difco Laboratories, Detroit, Mich.), 15 g; $H_2O$ to 1000 ml) supplemented with 100 μg/ml of kanamycin, and inspected to confirm production of fluorescent pigment. After this screening clones were grown overnight in LB broth, and then stored at −80° C. in 50% (v/v) glycerol for further studies.

Example 3

The following example describes a fungal in vitro inhibition assay. Inhibition of the growth of three root pathogens by Q8r1-96 recipient strains (transformed strains) prepared as described in Example 2, was conducted on potato dextrose agar (PDA) in petri plates. The method used was similar to that described by Thomashow and Weller, *Journal of Bacteriology* 170:3499–3508 (1988), except for the modifications indicated below. 3 μl of overnight LB broth cultures of bacterial strains were spotted on the surface of a plate of PDA, with two spots per plate on opposite sides and about 1 cm away from plate edge. A 0.5-cm plug from the leading edge of cultures of pathogens grown on PDA medium was place in the center of the plate. Plates were incubated at 28° C. and scored by measuring the distance between the edges of the bacterial colony and fungal mycelium. For inhibition of *Gaeumannomyces graminis* var *tritici*, bacterial broth cultures were spotted on the plates 24 hours after the fungal plug was placed, and the inhibition was scored 5 days after the bacteria were applied. For inhibition of *Rhizoctonia solani* AG8, bacterial broth cultures were spotted on the plates at the same time that the fungal plug was placed and the inhibition was scored 5 days later. For inhibition of *Pythium irregulare*, bacterial broth cultures were spotted on the plates 48 hours before the fungal plug was placed, and the inhibition was scored 2 days after the fungus was applied.

Results. The results are shown in Table 1, below. As can be seen from the data, the zones of inhibition of the transgenic strains Z30-97, Z32-97, Z33-97, and Z34-97 were significantly greater than that of Q8r1-96.

TABLE 1

In vitro inhibition of *Gaeumannomyces graminis* var *tritici*, *Rhizoctonia solani* AG8, and *Pythium irregulare* by parent strain *Pseudomonas fluorescens* Q8r1-96 and transgenic derivatives Z30-97, Z32-97, Z33-97 and Z34-97 on potato dextrose agar Size of Zone of Inhibition

| Strain | Ggt | Rhizoctonia | Pythium |
|---|---|---|---|
| *P. fluorescens* Q8R1-96 | 0.50 D | 0.17 B | 0.47 B |
| Z30-97 | 1.55 B | 0.55 A | 0.80 A |
| Z32-97 | 1.13 C | 0.53 A | 0.70 A |
| Z33-97 | 1.66 AB | 0.57 A | 0.67 A |
| Z34-97 | 1.70 A | 0.55 A | 0.73 A |

Means followed by the same letter are not significantly different, P = 0.05.

Example 4

The following example describes greenhouse screening bioassays. Materials and Methods.

Seed treatment: Seeds of spring wheat Penawawa were coated with different doses of the bacterial strains cultured on KMB (for Pseudomonas sp) or NBY (for Bacillus sp) and suspended in 0.5% methylcellulose. A bacterial suspension was spread evenly over the entire plate and cultered at 27° C. for 3 days. Three plates were prepared for each strain. Bacterial cells were harvested by scraping them into a capped centrifuge tube and washed twice with 40 ml sterile distilled water. Bacterial cells were resuspended into 15 ml of 0.5% ethylcellulose, and 10-fold dilution series was made with 0.5% methylcellulose. Twenty-five grams of wheat seed were thoroughly mixed with 9 ml of the bacterial—methyl cellulose suspension and air dried overnight. The real doses of bacterial cell on each seed were determined by dilution plate counts.

Greenhouse assay on disease suppression. A tube assay (Ownley et al., *Phytopathology* 82:178–184 (1992) and Weller et al., *Plant Disease* 69:710–713 (1985)) was used to test transgenic strains for suppression of take-all (caused by *Gaeumannomyces graminis* var *tritici* (Ggt)), Rhizoctonia root rot (caused by *Rhizoctonia solani* AG8), and Pythium root rot (by a complex of Pythium spp. including *Pythium iregulare*). Inoculum of each of these three pathogens was prepared by growing each pathogen individually on autoclaved whole oat grains respectively for 4 weeks (see U.S. Pat. No. 4,456,684 which is incorporated herein by reference). Inoculum was stored in the refrigerator until use. The assay used plastic tapered tubes (2.5 cm in diameter and 20 cm in length), with holes at bottom. The tubes were supported in a hanging position in plastic racks. Each tube was plugged with cotton balls and then filled half full with fine vermiculite followed by 13 grams of raw soil with or without ground oat inoculum. For tests on take-all and Rhizoctonia root rot, the soil was mixed with 1% (wt/wt) freshly ground oat kernel cultured inoculum (particle size: 0.25–0.50 mm). For tests on Pythium root rot, the soil was infested with one whole oat kernel colonized with *Pythium irregulare*. Then, 10 ml of water was added to each tube for Pythium infested soil, and 10 ml of water with metalaxyl (Ridomil 0.075 g/liter; Norvatis, Greensboro, N.C.) for Ggt and *Rhizoctonia solani* infested soil. After watering, tubes with the soil infested with *Pythium irregulare* and *Rhizoctonia solani* were incubated at room temperature for 48 hours before seeding. Tubes with the soil infested with Ggt were seeded immediately after watering. Two wheat seeds were planted in each tube, covered by a small amount of fine vermiculite and watered with 3 ml of water for Pythium test, or watered with metayl for Ggt and Rhizoctonia tests. Then, the tubes were covered with plastic for 3 days to retain soil moisture for germination and placed in a greenhouse with a 12-h photoperiod and a constant 16° C. for 4–5 weeks. After the emergence of the wheat seedlings (3–4 days), tubes were watered twice a week with 5 ml of ⅓ strength Hoagland's solution. All experiments were conducted in Quincy virgin soil obtained from Quincy, Wash., with 5–6 repeats and 5 tubes for each repeat. The severity of the three root diseases were evaluated after roots were washed free of the rooting medium. The severity of Rhizoctonia root rot was evaluated as the percentage of infected roots. The severity of Pythium infection was evaluated by the emergence and the height of seedlings. The severity of takeall was evaluated on a scale of 0 to 8 developed by Ownley et al., 1992, supra.

Statistical analyses. Results were analyzed by statistical software SAS (SAS Institute, Cary, N.C.). Emergence rate was analyzed after arcsine transformation of data. Disease rating data of take-all was analyzed by nonparametric statistics. The treatment means were separated by Fisher's protected least significant difference (LSD) at P=0.05.

Results. The results are shown in Tables 2–4, below. As shown in Table 2, transformed strains Z30-97, Z32-97, and Z34-97 at doses of $10^2$–$10^3$ CPU per seed reduced the percentage of wheat roots infected by *Rhizoctonia solani* AG-8 as compared to the parental strain Q8r1-96 at a similar dose, *P. fluorescens* 2-79 (the source of the phenazine-1-carboxylic acid genes) and the two nontreated controls. The parental strain Q8r1-96 is equivalent to Z30-97 and Z32-97 in suppression of Rhizoctonia only when Q8r1-96 is applied at a larger dose. As shown in Table 3, below, strain Z34-97 at a dose of $10^2$ CFU/seed is as effective at suppressing Pythium as the parental strain Q8r1-96 at a dose of $10^3$ CFU/seed. As shown in Table 4, below, strain Z34-97 provides significant suppression of *Gaeumannomyces graminis* var. *tritici* (Ggt). As shown in Tables 1–4 below, Z34-97 is able to suppress all three root diseases.

TABLE 2

Suppression of Rhizoctonia root rot of wheat (*Rhizoctonia solani* AG-8) by seed treatments of wild type and transgenic bacterial biocontrol agents.

| Treatment | CFU/seed[1] | Roots infected (%)[2] |
|---|---|---|
| Methylcellulose[3] | 0 | 60.7 a[4] |
| Nontreated[3] | 0 | 55.3 ab |
| *Pseudomonas fluorescens* 2-79[5] | $10^6$ | 48.9 b |
| *Pseudomonas fluorescens* Q8r1-96[5,6] | $10^3$ | 37.3 c |
| *Pseudomonas fluorescens* Q2-87[5] | $10^6$ | 34.8 cd |
| *Pseudomonas fluorescens* Q8r1-96[5,6] | $10^4$ | 30.8 cde |
| Bacillus spp. L324-92[5] | $10^7$ | 28.1 def |
| Transgenic Z32-97 | $10^2$ | 25.1 efg |
| Transgenic Z30-97 | $10^2$ | 25.1 efg |

TABLE 2-continued

Suppression of Rhizoctonia root rot of wheat (*Rhizoctonia solani* AG-8) by seed treatments of wild type and transgenic bacterial biocontrol agents.

| Treatment | CFU/seed[1] | Roots infected (%)[2] |
|---|---|---|
| Transgenic Z34-97 | $10^2$ | 21.6 fg |
| Transgenic Z34-97 | $10^3$ | 18.8 g |

[1]Seed were treated with bacteria suspended in 0.5% methylcellulose to give the indicated doses per seed.
[2]Percentage of roots with typical Rhizoctonia lesions were measured 4 weeks after planting.
[3]Methylcellulose treated seeds were treated only with 0.5% methylcellulose. Nontreated seed received no treatment.
[4]Means followed by the same letter are not significantly different, P = 0.05.
[5]Not in accordance with the invention, for comparison purposes only.
[6]Parent Strain.

TABLE 3

Suppression of Pythium root rot of wheat (*Pythium irregulare*) by seed treatments of wild type and transgenic bacterial biocontrol agents.

| Treatment | CFU/seed[1] | Emergence[2] |
|---|---|---|
| Methylcellulose[3] | 0 | 50 d[4] |
| Nontreated[3] | 0 | 54 cd |
| *Pseudomonas fluorescens* 2-79[5] | $10^6$ | 63 cd |
| *Pseudomonas fluorescens* Q8r1-96[5,6] | $10^3$ | 92 ab |
| *Pseudomonas fluorescens* Q2-87[5] | $10^6$ | 50 d |
| *Pseudomonas fluorescens* Q8r1-96[5,6] | $10^4$ | 71 bcd |
| Bacillus spp. L324-92[5] | $10^7$ | 92 ab |
| Transgenic Z32-97 | $10^2$ | 67 cd |
| Transgenic Z30-97 | $10^2$ | 67 cd |
| Transgenic Z34-97 | $10^2$ | 96 a |
| Transgenic Z34-97 | $10^3$ | 79 abc |

[1]Seed were treated with bacterial suspension in 0.5% methylcellulose to give the indicated doses per seed.
[2]Number of seedling emerging was determined 4 weeks after planting.
[3]Methylcellulose treated seeds were treated only with 0.5% methylcellulose. Nontreated seed received no treatment.
[4]Means followed by the same letter are not significantly different, P = 0.05.
[5]Not in accordance with the invention, for comparison purposes only.
[6]Parent strain.

TABLE 4

Suppression of take-all root rot of wheat (*Gaewnannomyces gruminis* var. *tritici*) by seed treatments of wild type and transgenic bacterial biocontrol agents.

| Treatment | CFU/seed[1] | Disease Rating[2] |
|---|---|---|
| Methylcellulose[3] | 0 | 4.2 a[4] |
| Nontreated[3] | 0 | 4.2 ab |
| *Pseudomonas fluorescens* 2-79[5] | $10^6$ | 3.9 abc |
| *Pseudomonas fluorescens* Q8r1-96[5,6] | $10^3$ | 2.9 e |
| *Pseudomonas fluorescens* Q2-87[5] | $10^6$ | 3.7 bcd |
| *Pseudomonas fluorescens* Q8r1-96[5,6] | $10^4$ | 2.9 e |
| Bacillus spp. L324-92[5] | $10^7$ | 3.5 cd |
| Transgenic Z32-97 | $10^2$ | 3.9 ab |
| Transgenic Z30-97 | $10^2$ | 3.8 abc |
| Transgenic Z34-97 | $10^2$ | 3.5 d |
| Transgenic Z34-97 | $10^3$ | 3.4 d |

[1]Seeds were treated with a bacterial suspension in 0.5% methylcellulose to give the indicated doses per seed.

TABLE 4-continued

Suppression of take-all root rot of wheat (*Gaewnannomyces gruminis* var. *tritici*) by seed treatments of wild type and transgenic bacterial biocontrol agents.

| Treatment | CFU/seed[1] | Disease Rating[2] |
|---|---|---|

[2]Take-all was evaluated on a scale of 0 to 8 (Ownley et al., 1992), where: 0, no disease evident; 1, <10% root area with black lesions; 2, 10–25% root area with black lesions; 3, >25% root area with black lesions and one root with lesions at base of stem; 4, = more than one root with lesions at base of stem; 5, all roots with lesions at base of stem, at least one lesion on lower stem, but no leaf chlorosis; 6, many lesions on stem and the first true leaf chlorotic; 7, all leaves chlorotic and plant severely stunted; 8, plant dead or nearly so.
[3]Methylcellulose treated seeds were treated only with 0.5% methylcellulose. Nontreated seed received no treatment.
[4]Means followed by the same letter are not significantly different, P = 0.05.
[5]Not in accordance with the invention, for comparison purposes only.
[6]Parent strain.

Example 5

This example describes root colonization of wheat roots by wild strains and transgenic strains.

Rhizosphere colonization. Rhizosphere colonization of trasgenic stains was characterized using the tube bioassay as described in the disease suppression assay above. Wheat seeds coated with bacterial cells of the test strains at a dose of $10^3$ CFU/seed were planted. The numbers of CFU in present on the seeds were determined at 66 hours and 1 week after planting by dilution plating on KMB media amended with rifampicin and cycloheximide at 100 μg/ml each.

Results. The results are shown in Table 5. As can be seen from the data, the transgenic strains of the invention reached the same population density as the parent strain 66 hours and one week after planting treated seeds.

TABLE 5

| Strain[a] | Days after planting | |
|---|---|---|
| | 66 hr (CFU × $10^7$/seed) | 7 days (CFU × $10^7$/g of root) |
| Pseudomonas fluorescens Q8R1-96 | 1.4 A[b] | 26.8 A |
| Z32-97 | 1.1 A | 11.7 A |
| Z33-97 | 1.1 A | 16.2 A |
| Z34-97 | 1.1 A | 16.0 A |
| Z30-97 | 1.5 A | 13.2 A |

[a]Wheat seeds were coated with a dose of $10^3$ CFU/seed.
[b]Means followed by the same letter are not significantly different according to Fisher's least significant test (LSD) at P = 0.05.

Example 6

The following example describes the physiological traits and substrate utilization patterns.

The exemplary parent strain *Pseudomonas fluorescens* Q8r1-96 was compared to *P. fluorescens* strain Q2-87 (which also has a locus for the antibiotic 2,4-diacetylphloroglucinol). The strains show physiological traits and substrate utilization patterns typical of *P. fluorescens* as described in Bergey's Manual (see Table 6, below).

TABLE 6

| | Q8r1-96 | Q2-87 |
|---|---|---|
| Gram stain | − | − |
| Shape | Rod | Rod |
| Fluorescent pigment | + | + |
| Oxidase | + | + |
| Arginine dihydrolase | + | + |
| Glucose fermentation | − | − |
| β-galactosidase | − | − |
| Gelatin hydrolysis | − | + |
| Denitrification | + | + |
| Utilization of: | | |
| D-glucose | + | + |
| L-arabinose | + | + |
| Sucrose | + | + |
| Propionate | + | + |
| Butyrate | − | − |
| Sorbitol | + | + |
| Adonitol | − | − |
| D-mannitol | + | + |
| N-acetyl-D-glucosamine | + | + |
| Maltose | − | − |
| D-gluconate | + | + |
| Caprate | + | + |
| Adipate | − | − |
| L-malate | + | + |
| Citrate | + | + |
| Phenylacetate | − | − |

Example 7

This example describes RAPD analysis to identify transformed strains with the characteristic banding pattern.

RAPD analysis with primer M13 was used to compare transformed strains with the parent strain Q8r1-96. Amplifiction of the DNA was carried out in a 25-μl reaction mixture, which contained 5 μl of a diluted heat-lysed cell suspension, 1×GeneAmp PCR buffer (Perkin Elmer Corp., Norwalk, Conn.) 200 μM each of dATP, dTTP, dGTP, and dCTP (Perkin Elmer), 80 pmole of primer M13, and 2.0 U of AmpliTaq DNA polymerase (Perkin Elmer). Each mixture was covered with one drop of mineral oil. Amplifications were performed in a Perkin Elmer Thermal Cycler 480. The PCR program consisted of an initial denaturation at 94° C. for 1 min 30 sec followed by 2 cycles of 94° C. for 30 sec, 36° C. for 30 sec, 72° C. for 2 min, followed by 40 cycles of 94° C. for 20 sec, 36° C. for 15 sec, 45° C. for 15 sec, 72° C. for 1 min 30 sec, followed by 1 cycle of 72° C. for 10 min. Samples (9 μl) of the PCR products were separated on a 2.5% agarose gel in 1×TBE buffer (90 mM Tris-borate, 2 mM EDTA (pH 8.3)) at 75 V for 5 hours. The gel was stained with ethidium bromide for 60 minutes, and the PCR products were visualized using a UV transilluminator.

The transformed strains Z32-97, Z33-97, Z34-97 share the following bands with parent strain *P. fluorescens* Q8r1-96: 330±20 bp; 600 bp±50 bp; 700±50 bp; 800 bp±50 bp; 900 bp±50 bp, and 1100 bp±60 bp. The transformed strain Z30-97 shares the following bands with its parent strain Q8r1-96: 600 bp±50 bp; 700±50 bp; 800 bp±50 bp; 900 bp±50 bp.

It is understood that the foregoing detailed description is given merely by way of illustration and that modification and variations may be made within, without departing from the spirit and scope of the invention.

What is claimed is:

1. A biologically pure culture of a strain of fluorescent Pseudomonas spp. bacteria which has a biosynthetic locus which encodes for the production of 2,4-diacetylphloroglucinol, which strain has been stably transformed with a DNA sequence which encodes for the biosynthesis of phenazine-1-carboxylic acid, whereby said transformed strain has the ability to produce both 2,4-diacetylphloroglucinol and phenazine-1-carboxylic acid.

2. The biologically pure culture of claim 1 which is further characterized as having bands at 600 bp±50 bp; 700±50 bp; 800 bp±50 bp; 900 bp±50 bp identified by Random Amplified Polymorphic DNA (RAPD) analysis using primer M13.

3. The biologically pure culture of claim 2 which is further characterized as having bands at 330 bp±20 bp and 1100 bp±60 bp.

4. The biologically pure culture of claim 1 wherein said strain is further characterized as having the ability to suppress root diseases in plants caused by the fungus Rhizoctonia.

5. The biologically pure culture of claim 4 wherein said strain is further characterized as having the ability to suppress root diseases in plants caused by the fungi *Gaeumannomyces graminis* (Gg) or Pythium.

6. The biologically pure culture of claim 1 wherein said fluorescent Pseudomonas strain has all of the identifying characteristics of *P. fluorescens* NRRL B-21905, NRRL B-21906, NRRL B-21907 or NRRL B-21908.

7. The biologically pure culture of claim 1 which further includes an agricultural carrier.

8. A method of controlling a root disease caused by Rhizoctonia, Pythium, or *Gaeumannomyces graminis* fungus (Gg) in plants susceptible to said root disease, which comprises growing said plant in the presence of an effective biocontrol amount of a biologically pure culture of a fluorescent Pseudomonas strain of claim 1.

9. The method of claim 8 wherein said plant is selected from the group consisting of small grain crop, turf grass or food, fiber or ornamental plant.

10. The method of claim 8 wherein seed of said plant is treated with an effective biocontrol amount of said strain prior to said growing.

11. The method of claim 8, wherein soil or furrow for growing said plant is treated with an effective biocontrol amount of said strain prior to said growing.

12. The method of claim 8 wherein said plant is treated with a bacterial treatment solution which comprises an effective biocontrol amount of said strain and a suitable liquid carrier.

13. The method of claim 8 wherein said Pseudomonas strain is a *P. fluorescens* strain having all of the identifying characteristics of NRRL B-21905, NRRL B-21906, NRRL B-21907 or NRRL B21908.

14. The method of claim 10 wherein said seed has a concentration of about $10^2$ to $10^5$ CFU per seed.

15. The method of claim 12 wherein said treatment solution has a concentration about $10^8$ to $10^{10}$ CFU per ml of solution.

16. The method of claim 8 wherein roots of said plant are dipped into a bacterial suspension of $10^2$ to $10^5$ CFU per ml of suspension.

17. An agricultural composition for controlling a root disease caused by Rhizoctonia, Pythium, or *Gaeumannomyces graminis* fungus (Gg) in plants susceptible to said root disease, said composition comprising a suitable carrier and an effective biocontrol amount of a biologically pure culture of a fluorescent Pseudomonas strain of claim 1.

18. The agricultural composition of claim 17 wherein said carrier is selected from the group consisting of water, buffer, methylcellulose, peat, and vermiculite.

19. The agricultural composition of claim 18 wherein said strain is in a concentration of about $10^8$ to $10^{10}$ CFU per ml of liquid carrier or $10^7$ to $10^9$ per gram of solid carrier.

20. The agricultural composition of claim 17 wherein said Pseudomonas strain is a *P. fluorescens* strain having all of the identifying characteristics of NRRL B-21905, NRRL B-21906, NRRL B-21907 or NRRL B- 21908.

21. A seed of a plant having applied thereto an effective biocontrol amount of a biologically pure culture of claim 1.

22. The seed of claim 21 where said seed has a concentration of about about $10^2$ to $10^5$ CFU per seed.

23. A stain of fluorescent Pseudomonas spp. which naturally produces 2,4-diacetylphloroglucinol, which strain has been transformed by stable introduction of a DNA sequence which encodes for the biosynthesis of phenazine-1-caroxylic acid, whereby said transformed strain has the ability to produce both 2,4-diacetylphloroglucinol and phenazine-1-carboxylic acid.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "M13 primer"

(iii) HYPOTHETICAL: NO (iv) ANTI-SENSE: NO (x) PUBLICATION INFORMATION:
      (A) AUTHORS: Keel, C
              Weller, D M
              Natsch, A
              DeFargo, G
              Cook, R J
              Thomashow, L S
      (B) TITLE: Conservation of the 2,4-Diacetylphloroglucinol
           Biosynthetic Locus Among Fluorescent Pseudomonas
           Strains From Diverse Geographic Locations
      (C) JOURNAL: Appl. Environ. Microbiol.
      (D) VOLUME: 62
      (E) ISSUE: 2
      (F) PAGES: 552-563
      (G) DATE: 1996
      (K) RELEVANT RESIDUES IN SEQ ID NO:1: FROM 1 TO 10

(xi) SEQUENCE DESCRIPTION: SEQ ID NO: 1:

GGTGGTCAAG      10

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Ph12a"

(iii) HYPOTHETICAL: NO (iv) ANTI-SENSE: NO (x) PUBLICATION INFORMATION:
      (A) AUTHORS: Raaijmakers, Jos M
              Weller, David M
              Thomashow, Linda S
      (B) TITLE: Frequency of Antibiotic-Producing Pseudomonas
           spp. in Natural Environments
      (C) JOURNAL: Appl. Environ. Microbiol.
      (D) VOLUME: 63
      (E) ISSUE: 3
      (F) PAGES: 881-887
      (G) DATE: March-1997
      (K) RELEVANT RESIDUES IN SEQ ID NO:2: FROM 1 TO 20

(xi) SEQUENCE DESCRIPTION: SEQ ID NO: 2:

GAGGACGTCG AAGACCACCA      20

(2) INFORMATION FOR SEQ ID NO: 3:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Ph12b"

(iii) HYPOTHETICAL: NO (iv) ANTI-SENSE: NO (x) PUBLICATION INFORMATION:
            (A) AUTHORS: Raaijmakers, Jos M
                         Weller, David M
                         Thomashow, Linda S
            (B) TITLE: Frequency of Antibiotic-Producing Pseudomonas
                       spp. in Natural Environments
            (C) JOURNAL: Appl. Environ. Microbiol.
            (D) VOLUME: 63
            (E) ISSUE: 3
            (F) PAGES: 881-887
            (G) DATE: March-1997

(xi) SEQUENCE DESCRIPTION: SEQ ID NO: 3:

ACCGCAGCAT CGTGTATGAG                                               20

(2) INFORMATION FOR SEQ ID NO: 4:

(i) SEQUENCE CHARACTERISTICS:
            (A) LENGTH: 7198 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Pseudomonas fluorescens (ix) FEATURE:
            (A) NAME/KEY: CDS
            (B) LOCATION: complement (1810..2859)
            (D) OTHER INFORMATION: /product= "PhlD"

(x) PUBLICATION INFORMATION:
            (A) AUTHORS: Thomashow, L S
                         Bangera, M G
            (B) TITLE: GenBank - U41818

(xi) SEQUENCE DESCRIPTION: SEQ ID NO: 4:

GTCGACCCAG TAAAGGCAGA CAATGCATGG CTCGCTGCTG ATGCTTTGGG CGTGGTAAGG      60

AATCTGCAAC GGGTCCCCGT CAGTCTTGAG CAATCGACCG TTGCCTTTGT AATACCAGGC     120

CTGTTCCGTC TTGGCGGTGC ACAGTGTGAT CTCGCTGACC TGAACAGCCA AGTTGTCATC     180

GGGTTTGAGC GGCGGCCTGT ATTTCGCGCC TGTGGGCGAG AGCGGATAGG GCGTCGATGG     240

GAGGCTCCTG AGGTAGGATT CCCAATCCAT GTTCAGGCGA GCGCAGTGGC TCAGGGCTTC     300

ATAAAGGTTT CCCTGCGGTG ATCGTACTTC CAGGCTTTGC CCGGATTTGA AGTCGAATAC     360

ACCCAGCCCG CGCAGCGGCT GCGGCGAGTC CAATAGCATT ACGTAATGCG TCATCACTTA     420

TCCTCCAGCG TCAAGCGAGC GGGCAGGGGG CCGTAGTCCG CACGGTCATT GAAAACAGGG     480

CTGGCTTCCT TGAGCCGCAG GGACAGCAAC CCGCCCATCA AACTACCAGC CAGTGCCAGA     540

AACAGAATGG CGGTAAGCCC CCAGTTCACG GCGATGTACC CGGCGACCAC GGGCGCAACG     600

```
CCACCGCCCA GGATTTCTCC GCAACCCACC ACCAGGCCCG TAGCGGTGGC CAGTAAACTG     660

GGTGGCACTG ATTCGCTGGT CAGTGGGCCG ACGGTGATGC AGATCAGGCT GAAATTGATG     720

AAAGATAAAA AGAACAGCTG GAGGAACAGT AGCCACGGTA ACGGCGGGGA AATGATGAGC     780

AAGCCGACCA GTAGTGTGCT GATCAGGAAG CAGATGGAAA CGACAGGCTT GCGGCCCAGT     840

TGGTCAGACA AACCGGGAAT GACGAGCTGG CCGAAAAAAC CACCCAGGCC GATCGCGGAG     900

ATGATCATGG CCATGGAGAA ATTGCTCAGG TGCAAGACGT CTGTCAGGTA GCTGGGGAGC     960

AGGGCGCACA GGACGAATTG GCACGTCAGT ATGCATAGCA TCAAGGCAAT GTTGAGGCGC    1020

ACGTTGCCGC TGGACAGGGC TGTTCGCCAT TGGCTGCCGG AGGGTTCTAC GAGCGGCCTT    1080

GGATGGGGCG CCTGGCTCGG TTGGTAGGTT CGATACAGAT ACCAGGCCAC CAGCAGGCCC    1140

GGCAACGAGA TGATGGCGAA CACGGCGCGC CACGATCCGA ACATTTCAAA CAATACGCCC    1200

GCCAGCAGCG GCCCCAGGCA CAGGCCGATG ATGGGAAACA GTGCCTGCTG GATGCCCAGG    1260

TTGAGCCCGC GTCGGCACGG CTGCGAAACT TCATCGGTGA CAATGATGCT GACCGGGGTG    1320

AAGGCGCCTT CGCAGATCCC CATCAAGGCG CGCAGGAGCA CCAGGCCCAT AAGGCTTGAG    1380

ATCAACGCAG ATGCGCCGGC CAGGAGCGAT ACCAAGGTAA TCGAAAGCAC CAGCAGTTGC    1440

TTGGTGCCCA ATCGCCTGAT AGCAACGCCC ATGAAGAGGG CCGAGCCTCC CCAGGCAAAT    1500

GCCAGGATCG CCGATAACAG GCCCAGGTCC TGATAGTCCA GGGCCAGGTC ATGCATGATC    1560

ACCGGGAACA ACGGCATGAT AATGAATCGA TCAAGTCCTA CCAGCCCGAA GCTCAGCGAC    1620

AAAAGAACGA CCATGCGTCT TTCGTAGCCA CCCCAAGGTC GAGTGGCAAG ATACGTACTC    1680

TCCATGTTCT TCCCCTTCTT TCCTTAGCCC TTTCGACGTT TTCTCGAAAC GGGTGAACGC    1740

TTGTGTTCGA TACTCCTGTA GCCAGGGGCG GATCCGCCCC CGGCTTGGTG CGTGCAATGT    1800

GTTGGTCTGT CAGGCCACCC ACTTGCCCAC GGCCATTTCA GCTGTGAAGC CAGGGCCGAA    1860

GGCTGCCAGC ATGCCGGTCG CTCCATTGGC CGGCCCGCTG TCGAACTGGC GCTTGAGGAC    1920

GTCGAAGACC ACCACGCTGG CAATATTGCC GGCCTCGCTC AAGCTGTCGC GAGACTGCGC    1980

GACCCTGCCA GGTTCCAGAT CGAGCTGCAG CACCAGCTCA TCAAGAATTT TTCGTCCACC    2040

GGTGTGGAAG ATGAAAAAGT CATTTTGAGC GCAATGTTGG TTGAAGGTCT CGAAGTTCAA    2100

TTCCTCCATC ATCGGGGCCA CGTCTTTAAT GGAGTTCATG ACGGCTTTGT CCAGGGTGAA    2160

GTGAAAGCCG CTGTCCTTGA CGTCATATTT AATGTAGTGC TCGCTGTCAG GCAGGAAATA    2220

AGAGCCGGTT TTGGCGATCT TGAATCCCGG CGCCTTATCG TCGGCGCGCA TTACGCAGGC    2280

CGAGACGGCA TCGCCGAACA GCGCTGCGGA TATGAACGCG TGCAACTTGG TGTCCTGTGG    2340

TTGATAGCAG AGTGACGAGA ACTCCAGCGA GACAATAAGG GCGTGGTTGT CTGGAGACAG    2400

GCTGGCAAAG TCGTTGGCTC GATTAATCGC CGCGGCGCCT GCCACGCATC CCAATTGAGC    2460

GATCGGCAAT TGTACGGTCG ACGTTCGCAG TCCCAAGTCA TTGATCAGGT GGGCTGTCAG    2520

CGATGGCATC ATGAACCCGG TGCAAGAGGT AACGGCGACC ATCCGGATGT CGTCCGTGGT    2580

CAAGCCCGCG TTTTCAATGG CCTGGCGCGC GGCGATTGAA GACATGCGGC GAGCCTCTCG    2640

CTCATACACG ATGCTGCGGT GGGTAAAGCC GGTATGCACC GCAAGTTCAT CGATGGGCAA    2700

GACCAGATAC CGTTCATTGA CTTGGGTGTT TTGAATCATC CGTTTAGCCA ATGCCATGCG    2760

CGGATGATCG TCATGCAACT GTTCCAAGTG ATCGATCATC TGTTGTTGGG TAATTTTGTA    2820

ATGCGGGAAA AGCAAGCTGG GTTTGCAAAG AGTAGACATG ACAAGTCCTC GGCTGAAAGC    2880

CAATAAAGAG TAGAAAACCA CGTTTAAGGC AATGGCAAAG CAGGACTCTG AAAAGCAGAA    2940
```

```
TCAAACAACG GGCCGGTTGG CCGGAAATAG CGACTGTTGT TATGGATGGC GCGGTATGCA    3000

GCAGTAACTT GTTTGTTATT TCGCCAATAC GAATTTATAA GCGTATTGCC ACGCCAGGTT    3060

GCTTTCCCGA ACGTGCTTGC GAATAACCAT TCGCACTGGT GCTCCAGTCA CGACTTGCCG    3120

GGGATCGACG ACATCGACGA TTTCCGAGGC GATCACCAAG CCATCGTCCA GGCGCACCAT    3180

TGCCATGAAG CGCGGGACGG TTTCGCCATA TCCCATGGCC GCGAGAATGG GGTTTTCAGC    3240

ATGGGCGCTG ACCTGGATCG TGCCGGTGCG TGCGCAGCGA TACGGTTCCA CGTTCAATGA    3300

GTTGCATGCG CCGCAGACGG TGCGCCGTGG GAAGAAGATT TCTTCGCAAT CCTGGCAGCG    3360

GCTGCCTTCG AGACGATATT TTCCGCCATG TTCGCGCCAT TCGCGCAACA TGCTGGCGGT    3420

GGTCATGCGG TGTATTTGTT CTGGGTAAAG GGACATGGTC GGCTCCTTAA TCGTTGGAAA    3480

GCACAATGAC GCTGTTATGC GCGGCGTAAC CGCCCAAGTT CTGCGAGACG CCAATGCGAG    3540

CGTCCTTGAC TTGGTTGTTG GACTCGCCGC GAAGTTGTCG GAACAGCTCG GTAATGTGCA    3600

GGATGCCGTC GCAACCAGAG GCGTGGCCGC GGCCAATATT GCCGCCATCG GTGTTTAATG    3660

GCAGTTGCCC GTCGAGGGCT ATGCCGCCTT CCAATACAAA GTCGCCTGCC TGGCCTGGAC    3720

CACATACGCC CATGGATTCC ATCTGAATCA ATCCGGCACC CAGCAAGTCG TAGACTTGGG    3780

CCACATCGAT ATCCTTGGCG GTGATGCCGG CTTTTTTGTA GGCGATTTCG GCGCAAGCAA    3840

TGGAGTTGGC GGAAACCGCC ATGCCGACGT CTTTTGGCAG GCCTGGATAT TTCAGGGTCG    3900

GGTTGTGATA GCGCGTCCCG AAATAATGGG ATACGCCGGT ATAGGCACAA CCACGGACGA    3960

ATACCGGTTG GGTCGTGTAG CGGTGCGCCA GGTGTTCGGC GACCAGGATG GCGCAACCGC    4020

TGGCTTCACC CCAGGCCAGC ATCGAGCCAC ATGCTTCGCT GTTCTTGAGG GTTTCAAGGG    4080

ATGGCACCGG CACGCCATAG CGGGTTGCCG TGGGCGTGTT GTGCGCATAG ATGCGCATTT    4140

GCCGACCAAA CGTTGCCAGG ACATCCGCTT CGCGTCCTGC ATAGCCAAAT TTTTCAAAAT    4200

ATTCGGCGGT TGCGAGGGCA AAGGCGTCGG TGTGCGAAAT GCCCAGGAAA TAATCGTACT    4260

CACATTCGGT ACTGGAGCCG ATGTATTCGG CATAGTTGAA GTGGTCGGTC ATTTTTTCAA    4320

AGCCACCACA CAGGACGATG TCGTACTCAC CCGAGGCGAC CATCTGATGG GCCATCTGAA    4380

AGGAAACCGA GCTGCTGGTG CAGTTGGCAG TGCTCATGAA CGTCGGGCA GGGCTGATGC    4440

CCAGGGCATC GGAAATAGTC GGGCCCAGGC CGCCGTATTC GGAAATACCT TCACCGTGAT    4500

ATCCATAAGC GACTGCCTGA AGTTCACGGG GATGCATCTT GATGGCGTTG AGCGCCTGAT    4560

AGGCGGACTC GACGATCATC TCCTTGAAGG TTTGACGGAC TCTGGAGCTG CCGGGTTTGG    4620

AAGTATAGGC AGCCGAAACG ATAGCAACGC GTCGTGCGCT CATTGGAAGT GCTCCTTGCT    4680

GGATGGTTGG GAATCAGAGG TAGGCTGTCA GGGCGTAGTC AGGCCGCAAG TATTTGAACT    4740

CGTACTTGAT CGACGTCCCG TAATCCACGT AATACTTGTC TTCCAGCAGC GTGCGCAGCG    4800

CAACGTTGGT CTTTTGGTAG GCTTCGATGG CATCGGTCAC TGTCAACGCA ATCGCATCGC    4860

TGCCCGCACC AAACCCGTAC GACACCAAGA GGATTTTTTC ACCCGGACGC GCTCGGTCCA    4920

GTACGCTCAC CAAGCCCAGC AACGGACTCG CGGCCCCCGC ATCACCGACA CTCTGGGCAT    4980

AAATGCCAGG TTCGATCTGC GCTTTGGTGA AGCCCAGGCC TTTGCCAAGA GAGAAGGGGG    5040

TCGAAACCAG GTTTTGCTGG AATACGACAT AGTCGAAATC GCTGGCCTGT ACATTCATCT    5100

TGGCCATCAA TCCCGACGCA GCACGATGGG TCTGGTCTTC AAGGCCAATG CTGTTCTTGT    5160

CGGAGCCCAG CCCCATTCCT GAGCGAATGT AGCGGTCTCC CTGGGGCGG ATGTTGTCAG    5220

CCACATCGGC GGCGCAAGAA AAGCTGGCAT CGAAATGCGC GATCACATTT TCAGTACCCA    5280

ACAACAGTGC GGCGGCTCCC GCTCCGGCGT AGGACTCGGT CAAGTCGCCG GGGCGGTGT    5340
```

```
TGCGGTTGAT CGTATCGGCG CCTATTGCCA GTGCATTGCC GGCCATGCCC GAGGCTACCA    5400

GGGCATAGGC GATCTGCAGG GCGCTGGTGC CTGATTTGCC GGCAAACTGT ACGTCCGCGC    5460

AGAAGGCGTC ATAACCGCAG CCGAGCATTT CCAGAATGAC CGCGGCCGAG GCGCGGGAGT    5520

CATATGGGTT GGTGCACGTA CCCAGGTACA GCGCTTCCAG GTCGCAAGAA GGGGCTTTGT    5580

CCAGCGCACG TTGAGCGGCC AGGACACTCA AGGTAATGAC GTCCTCATCG GGTTGGAGTA    5640

CAGCCCTTTC AACGACGCCC AGTTGGTTGG TGACCAGACT CAAGTCTGTG TTTTTCCAGA    5700

CGTGGATCAC GTCTTCCACT TTAAGGCGGC ACACCGGGAT GCCCGCGCCA TAGCTCACAA    5760

TTCCTACTTT ATTCACGTGT ACTTCCTCCA GATTCCTTTC TTCACCTGCC AGCGGATAGC    5820

CGTGACCGAT GCATGAAATA TTTAGAAACT ATCTAACGGT GCCCGCAAAG TGTCGTTGGC    5880

AGTCCTATGC CCGGAAATCG GGCTCCTCAA GGGGAAAAC TACAGTTCCT TTGAGGGAGA    5940

ACGGGTTTAT TATCCTTCTA TTATTATGTA TGATACGAAA CGTGCCGTAT CGTTAAGGTC    6000

TTGTTAAAAA TTGATGACTA TTTATCGGGT TTCTTCCTAT CTAGTGGCAA GTTCCGCTAT    6060

TGAGGTGTGC AGTAAGCAG AAACTTAGAT CATAAAAACA TACAAAACGA AACGATCCGT    6120

TTCATTGCTT TTCGAGAGAA TCCTATACCT TGCGTCTCTT TTGTCAAGCG CCATATTGGA    6180

GATTTTGAAT TATGGCCCGT AAACCGTCTC GGAGCTCCAT TGGCTCATTG AGGAGCCCAC    6240

ATACGCACAA AGCGATCATC ATCTCCGCTA TAGAAACACT CAAGGAGTGC GGTTATTCAG    6300

GGTTGAGTAT CGAGGCTGTG GCTCGCCGTG CCGGCGCGAG CAAGCCGACC ATCTATCGAT    6360

GGTGGGGTAA CAAGGCGGCT TTGATCGCCG AAGTCTACGA GAGCGAAAGC GAGCAGATTC    6420

GCAAGGAGCC TGATAAAGGA TCCTTCAAGG AGAACCTCAA TTTCCTGCTG CTCAATCTGT    6480

GGAAGGTCTG GAGAGAAACG ATTTGCGGGG AGGCGTTTCG GTGTGTCATC GCTGAAGCCC    6540

AGCTCGACCC CAGTACGCTG CCCAAGCTGA AGGATGAATT CATGGAGCGT CGTCGGGAAT    6600

TGCCGCGAAA GCTGGTGGAA AACGCCATCC AGCAAGGTGA GTTGCCCAAG GACACGTCCC    6660

GTGAGTTGTT GTTGGACATG ATCTTCGGAT TTTGCTGGTA CAGGCTGTTG ACTGAGCAAC    6720

TGGAAGTGGA GGGTGACATC AATGAATTCA CGACGCTTCT GTTGAACGGC GTGTTGCGTA    6780

CGACTTCGGC GGCGGAGTAA GGCGCCGCCG AAGCCTGTTC AAGGGTGAGG ATTGGCCTTA    6840

CGCCGCGCCG CTGAACTGTG CATGAAGGCC AGGCAGGATA CTGGCCAGGT GGTTGAACTC    6900

ACACAGATCA TGCACAGCAA ATTCATAAGC CAGGGTTTCC AGTTCGGCTT CCCCAAACCC    6960

GTTTTCCTTC AACAACTGCG CGGCGCGTTC GGCACCGGGA AAACGCAGCA TCGCTGGGTG    7020

GCTGCCCACC CAGTAACGGC TGGTCAGGTA CAAGCCTTCG GGGCATTCCT TGAACAAGTG    7080

CACCATGAGC GATATCGGCA CTTGCGGCTG ATCCGCCAGG CTCATCAAGG CGCTGACGCT    7140

GCCGTCTATT TTTGATTCGC GATACAGGTC CGCAGAGAAA CCCAGCTCGC ATGGATCC     7198
```

(2) INFORMATION FOR SEQ ID NO: 5:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Ser Thr Leu Cys Lys Pro Ser Leu Leu Phe Pro His Tyr Lys Ile
 1               5                  10                  15

Thr Gln Gln Gln Met Ile Asp His Leu Glu Gln Leu His Asp Asp His
```

-continued

```
                    20                  25                  30
Pro Arg Met Ala Leu Ala Lys Arg Met Ile Gln Asn Thr Gln Val Asn
            35                  40                  45
Glu Arg Tyr Leu Val Leu Pro Ile Asp Glu Leu Ala Val His Thr Gly
     50                  55                  60
Phe Thr His Arg Ser Ile Val Tyr Glu Arg Glu Ala Arg Arg Met Ser
 65                  70                  75                  80
Ser Ile Ala Ala Arg Gln Ala Ile Glu Asn Ala Gly Leu Thr Thr Asp
                85                  90                  95
Asp Ile Arg Met Val Ala Val Thr Ser Cys Thr Gly Phe Met Met Pro
            100                 105                 110
Ser Leu Thr Ala His Leu Ile Asn Asp Leu Gly Leu Arg Thr Ser Thr
            115                 120                 125
Val Gln Leu Pro Ile Ala Gln Leu Gly Cys Val Ala Gly Ala Ala Ala
    130                 135                 140
Ile Asn Arg Ala Asn Asp Phe Ala Ser Leu Ser Pro Asp Asn His Ala
145                 150                 155                 160
Leu Ile Val Ser Leu Glu Phe Ser Ser Leu Cys Tyr Gln Pro Gln Asp
                165                 170                 175
Thr Lys Leu His Ala Phe Ile Ser Ala Ala Leu Phe Gly Asp Ala Val
                180                 185                 190
Ser Ala Cys Val Met Arg Ala Asp Asp Lys Ala Pro Gly Phe Lys Ile
            195                 200                 205
Ala Lys Thr Gly Ser Tyr Phe Leu Pro Asp Ser Glu His Tyr Ile Lys
    210                 215                 220
Tyr Asp Val Lys Asp Ser Gly Phe His Phe Thr Leu Asp Lys Ala Val
225                 230                 235                 240
Met Asn Ser Ile Lys Asp Val Ala Pro Met Met Glu Glu Leu Asn Phe
                245                 250                 255
Glu Thr Phe Asn Gln His Cys Ala Gln Asn Asp Phe Phe Ile Phe His
                260                 265                 270
Thr Gly Gly Arg Lys Ile Leu Asp Glu Leu Val Leu Gln Leu Asp Leu
            275                 280                 285
Glu Pro Gly Arg Val Ala Gln Ser Arg Asp Ser Leu Ser Glu Ala Gly
    290                 295                 300
Asn Ile Ala Ser Val Val Val Phe Asp Val Leu Lys Arg Gln Phe Asp
305                 310                 315                 320
Ser Gly Pro Ala Asn Gly Ala Thr Gly Met Leu Ala Ala Phe Gly Pro
            325                 330                 335
Gly Phe Thr Ala Glu Met Ala Val Gly Lys Trp Val Ala
            340                 345
```